United States Patent
Chen et al.

(10) Patent No.: US 7,329,764 B2
(45) Date of Patent: Feb. 12, 2008

(54) SUBSTITUTE BENZOTHIOPHENE COMPOUNDS

(75) Inventors: Zhidong Chen, New Milford, CT (US); John David Ginn, New Milford, CT (US); Eugene Richard Hickey, Danbury, CT (US); Weimin Liu, Sandy Hook, CT (US); Can Mao, New Milford, CT (US); Tina Marie Morwick, New Milford, CT (US); Peter Allen Nemoto, Southbury, CT (US); Denice Spero, West Redding, CT (US); Sanxing Sun, Danbury, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 225 days.

(21) Appl. No.: 10/902,562

(22) Filed: Jul. 29, 2004

(65) Prior Publication Data

US 2005/0038104 A1 Feb. 17, 2005

Related U.S. Application Data

(60) Provisional application No. 60/491,575, filed on Jul. 31, 2003.

(51) Int. Cl.
*C07D 333/00* (2006.01)
*A61K 31/38* (2006.01)

(52) U.S. Cl. .......................... 549/49; 514/443
(58) Field of Classification Search ............ 536/44
See application file for complete search history.

(56) References Cited

U.S. PATENT DOCUMENTS

| 5,350,748 A | 9/1994 | Boschelli et al. |
| 5,852,046 A | 12/1998 | Lang et al. |
| 2004/0053957 A1 | 3/2004 | Cywin et al. |
| 2004/0180922 A1 | 9/2004 | Cywin et al. |

FOREIGN PATENT DOCUMENTS

| WO | WO 95/34548 | 12/1995 |
| WO | WO 02/41843 | 5/2002 |
| WO | WO02051849 | 7/2002 |
| WO | WO 03/037886 A2 | 5/2003 |
| WO | WO 03/072561 A1 | 9/2003 |
| WO | WO 03/103661 A1 | 12/2003 |

OTHER PUBLICATIONS

Sausville et al. Contributions of human tumor xenografts to anti-cancer drug development. Cancer Research, 2006, vol. 66, pp. 3351-3354.*
Johnson et al. Relationaships between drug activity in NCI preclinical in vitro and in vivo models and early clinical trials. British J. of Cancer, 2001, 84(10):1424-1431.*
Vitali, T., et al. "Proprieta Biologiche di Composti 1,2-benzisotiazolici" Ateneo Parmense Acta Naturalia, vol. 7, No. 1, 1971, pp. 71-109, XP009040652.
Stewart, W., et al. "Fused Thieno[3,2-d]-v-Triazine-4(3H)-Ones", HETEROCYCLES, vol. 3, No. 2, 1975, pp. 135-138 XP009040651.
Beck, J.R., et al., "Synthesis of [1]Benzothieno[3,2-d]-v-triazine Derivatives. A Unique Diazonium Ion Cyclization"J.Org.Chem., vol. 41, No. 10, 1976, pp. 1733-1734, XP002244950.
Market, J., et al. "Neue Synthesen Mit Elementarem Schwefel Darstellung Von 1,2-Benzisothiazolen und Einige Folgereaktionen-"(New Synthesis with Elemental Sulfur—Preparation of 1,2-Benzisothiazoles and some Secondary Reactions) Liebigs Ann. Chem., vol. 5, 1980, 768-778, XP000567752.
Abdel-Hafez, A. A., et al. "New Benzothiophene Derivatives I. A Convenient Synthesis of Novel Benzothienotriazines"; Bull.Fac. Sci., Assiut Univ., 22 (2-B), pp. 63-78 (1993).
P. Cirillo, et al. "Substituted 3-Amino-Thieno[2,3-b]Pyridine-2-Carboxylic Acid Amide Compounds and Processes for Preparing and Their Uses" U.S. Appl. No. 10/730,172, filed Dec. 6, 2003.
C. Cywin, et al. "Substituted Tricyclic Heterocycles and Their Uses" U.S. Appl. No. 10/960,550, filed Oct. 7, 2004.

* cited by examiner

*Primary Examiner*—Ardin H. Marschel
*Assistant Examiner*—James D. Anderson
(74) *Attorney, Agent, or Firm*—Michae Morris; Mary-Ellen M. Devlin; Anthony P. Bottino

(57) ABSTRACT

Disclosed are compounds of the formula I shown below, wherein R1, R2, R3 and R4 are described herein, which are active as anti-inflammatory agents. Also disclosed are methods of using and making such compounds

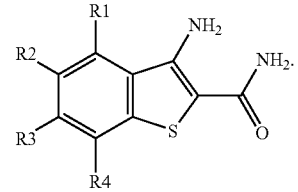

Formula I

3 Claims, No Drawings

SUBSTITUTE BENZOTHIOPHENE COMPOUNDS

RELATED APPLICATION DATA

This application claims benefit to U.S. provisional application No. 60/491,575 filed Jul. 31, 2003.

TECHNICAL FIELD OF THE INVENTION

This invention relates to benzothiophene compounds of formula I.

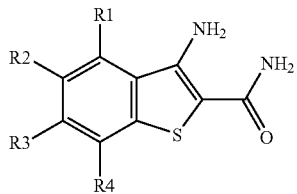

Formula I

The compounds are useful in the treatment of IKK mediated diseases including autoimmune diseases, inflammatory diseases and cancer. The invention also relates to processes for preparing such compounds and pharmaceutical compositions comprising them.

BACKGROUND OF THE INVENTION

NF-κB or nuclear factor κB is a transcription factor that induces the expression of a large number of pro-inflammatory and anti-apoptotic genes. These include cytokines such as IL-1, IL-2, TNF-α and IL-6, chemokines including IL-8 and RANTES, as well as other pro-inflammatory molecules including COX-2 and cell adhesion molecules such as ICAM-1, VCAM-1, and E-selectin. The NF-κB family includes homo- and heterodimeric transcription factors composed of members of the Rel family (see for example P. A. Baeurle and D. Baltimore, *Cell*, 1996, 87, 13). Under resting conditions, NF-κB is present in the cytosol of cells as a complex with IκB. The IκB family of proteins serve as inhibitors of NF-κB, interfering with the function of its nuclear localization signal (see for example U. Siebenlist et al., *Ann. Rev. Cell Biol.*, 1994, 10, 405). Upon disruption of the IκB-NF-κB complex following cell activation, NF-κB translocates to the nucleus and activates gene transcription. Disruption of the IκB-NF-κB complex and subsequent activation of NF-κB is initiated by degradation of IκB.

Upon cellular activation by a variety of pro-inflammatory stimuli including IL-1, TNF-α and LPS (bacterial lipopolysaccharide), two specific serine residues of IκB are phosphorylated. Upon phosphorylation, IκB undergoes polyubiquination and subsequent degradation by the 26S proteasome (see for example V. J. Palombella et al., *Cell*, 1994, 78, 773), freeing NF-κB to translocate to the nucleus. The phosphorylation of IκB is carried out by the IκB kinases (see for example a review by M. Karin and M. Delhase, *Seminars in Immunology*, 2000, 12, 85). The traditional IKK complex includes at least three subunits, IKKα (also called IKK-1), IKKβ (or IKK-2) and IKKγ (or NEMO), although other relevant complexes involving IKKα and IKKβ may exist. IKKα and IKKβ are both catalytic subunits while IKKγ is believed to be a regulatory subunit. Both IKKα and IKKβ can phosphorylate IκB. For the purposes of this document, the terms IKK or IKK complex refers to any complex that has kinase activity derived from IKKα and/or IKKβ subunits.

In vivo, activation of IKK occurs upon phosphorylation of its catalytic subunit. Both IKKα and IKKβ can be phosphorylated on serine residues, S177 and S181 of the activation loop in the case of IKKβ, and S176 and S180 of the activation loop for IKKα. An βIKK mutant having alanines in place of serines at 177 and 181 prevented IKKβ phosphorylation and subsequent activation of the IKK complex by TNFα, IL-1 and other upstream activators. These results support a key role for IKKβ in phosphorylation of IκB following proinflammatory stimulation.

Studies in which the NF-κB pathway has been inhibited in cells and animals support the concept that inhibition of the phosphorylation of IκB is a viable approach to treatment of inflammatory, autoimmune and other diseases. Transgenic expression of the IκB inhibitor in T cells caused a significant reduction in the severity and onset of collagen-induced arthritis in mice (R. Seetharaman et al., *J. Immunol.* 1999, 163, 1577). These experiments indicate that suppression of NF-κB in the diseased joint could reduce both the severity and progression of rheumatoid arthritis. In primary intestinal epithelial cells, the NF-κB inhibitor blocked the expression of IL-1, IL-8, iNOS and COX-2, mediators that are up-regulated during the course of inflammatory bowel disease (C. Jubin et al., *J. Immunol.*, 1998, 160, 410). Expression of this inhibitor in certain tumor cells enhances killing of these cells by chemotherapeutic reagents (A. A. Beg and D. Baltimore, *Science*, 1996, 274, 782).

Analysis of biopsies from lungs of patients with chronic obstructive pulmonary disease (COPD) found an increased expression of NF-κB that correlated with disease severity (A. Di Stefano et al., *Eur. Resp. J.*, 2002, 1, 437). Inhibition of NF-κB activation with inhibitors of IKK-β was among the anti-inflammatory approaches reported to be potentially useful in the treatment of COPD (P. J. Barnes, *Nature Rev. Drug Disc.*, 2002, 1, 437). Likewise, inhibition of NF-κB activity has been mentioned as a therapeutic approach for asthma (A. Pahl and I. Szelenyi, *Infl. Res.*, 2002, 51, 273).

Recent reviews suggest an essential role of inflammatory mediators in the development of cardiovascular disease. The inflammatory mediators and the cells that they recruit are reported to play a key role in the development of fatty streaks and plaques that lead to atherosclerosis. In addition they are reported to play a key role in subsequent degradation of the fibrous cap that forms over the plaque, leading to rupture and clot formation. If the clot grows large enough it can lead to myocardial infarction or stroke. Thus, anti-inflammatory drugs that can inhibit the production of these mediators and subsequent recruitment and activation of these cells may be beneficial in treatment of these diseases (P. Libby, *Scientific American*, 2002, 46).

A number of studies indicate that activation of NF-κB also plays a key role in the pathogenesis and development of cancer (see for example reviews by B. Haefner, *Drug Disc. Today*, 2002, 7, 653 and M. Karin et al., *Nat. Rev. Cancer*, 2002, 2, 301). Studies have shown that cells in which NF-κB is constitutively active are resistant to apoptosis. This can contribute to carcinogenesis by preventing cell death in cells that have undergone chromosomal changes or damage. In addition tumor cells with constitutively active NF-κB are resistant to anti-cancer therapies including chemotherapy and radiation. Further studies have linked activated NF-κB to a variety of lymphoid-, myeloid- and epithelial-derived malignancies including leukemia, lymphomas and breast, gastric, colorectal, lung, and pancreatic cancers. Thus, it is suggested that inhibitors of NF-κB, including inhibitors of IKKα and IKKβ, may be useful either alone or in combination with other anti-cancer therapies in treating cancer.

Studies have also been done in mice with targeted disruption of the IKKβ gene. Knockout of the IKKβ gene resulted in embryonic lethality due to apoptosis of hepatocytes. However, fibroblasts from the IKKβ knockouts did not undergo IKK and NF-κB activation upon stimulation with IL-1 or TNFα (Q. Li et al., Science, 1999, 284, 321), supporting a key role for IKKβ in and NF-κB activation following inflammatory stimuli.

A conditional knockout was generated by expressing a liver-specific inducible dominant negative IκBα transgene (I. Lavon et al., Nature Medicine, 2000, 6, 573). These mice were viable with no signs of liver dysfunction even after one year but they did have impaired immune function. This study supports the idea that inhibition of IKKβ can result in immune suppression without damage to the liver.

IKKα knock-out mice died shortly after birth and displayed a variety of skeletal defects and skin abnormalities. Fibroblast and thymocytes from these mice showed normal IKK activation and IκB degradation in response to TNFα, IL-1 or LPS (Y. Hu et al., Science, 1999, 284, 316; K. Takeda et al., Science, 1999, 284, 313). Recent studies with knock-out and knock-in mice have revealed distinct roles for IKKα in development and cell signaling. In contrast to the studies with IKKα knock-out mice, mice having a kinase inactive version of IKKα knocked in are viable and fertile, indicating that the perinatal lethality and abnormalities seen in the IKKα knock-out mice are not due to the lack of kinase activity. However, these mice do have defects in B cell maturation and development of secondary lymphoid organs (U. Senftleben et al., Science, 2001, 293, 1495). This phenotype appears to be due to a defect in processing of the NF-κB2/p 100 protein to p52, the DNA binding form of this member of the Rel family of transcription factors. In turn, this leads to a defect in the activation of a subset of NF-κB target genes in B cells. In addition, other studies with these same mice have shown that IKKα kinase activity is required for NF-κB activation in the mammary epithelium during pregnancy (Cao, Y., et. al., Cell, 2001, 107,763). This pathway is specifically activated through the TNF receptor family member RANK, requires phosphorylation of the canonical IKK substrate IκBα, and culminates in induction of the cell cycle regulatory gene Cyclin D1.

These studies indicate that an inhibitor of IKKα kinase activity may be useful in treating diseases associated with inappropriate B cell activation such as lupus (O. T. Chan et al., Immunological Rev., 1999, 169, 107) and rheumatoid arthritis (A. Gause and C. Borek, Biodrugs, 2001, 15, 73). In addition, an inhibitor of IKKα may be useful in the treatment of breast cancer since NF-κB is constitutively active in a number of breast tumors and many of these tumors depend on Cyclin D1 for proliferation.

Collectively, the studies described above provide support that inhibition of NF-κB function through inhibition of IKK may be a useful therapeutic approach to treatment of autoimmune and inflammatory diseases, cardiovascular disease and cancer.

Some inhibitors of IKKβ have been reported. U.S. provisional application No. 60/386,312, U.S. provisional application No. 60/457,867 and U.S. non-provisional application Ser. No. 10/453,175 describe substituted 3 amino-thieno[2-3-b]pyridine-2-carboxylic acid amide compounds. WO 01/58890 describes heteroaromatic carboxamide derivatives as inhibitors of IKKβ. WO 01/68648 describes substituted β-carbolines having IKKβ inhibiting activity. Substituted indoles having IKKβ inhibitory activity are reported in WO 01/30774. WO 01/00610 describes substituted benzimidazoles having NF-κB inhibitory activity. Aspirin and salicylate have been reported to bind to and inhibit IKKβ (M. Yin et al., Nature, 1998, 396, 77).

Substituted thienopyridines having cell adhesion inhibiting activity are reported in U.S. 2001/0020030 A1 and A. O. Stewart et al., J. Med. Chem., 2001, 44, 988. Thienopyridines exhibiting gonadotropin releasing hormone antagonizing activity are reported in U.S. Pat. No. 6,313,301. Substituted thienopyridines described as telomerase inhibitors are disclosed in U.S. Pat. No. 5,656,638.

Substituted benzothiophenes have been reported. WO 95/34548 describes a process for making substituted benzothiophenes. U.S. Pat. No. 5,852,046 describes a series of antirrhythmic susbstituted benzothiophene containing compounds containing guanidine. U.S. Pat. No. 5,350,748 describes substituted benzothiophene compounds as potential inhibitors of inflammatory disease WO 200241843 describes substituted benzothiophene compounds having acyl hydrazine moieties that are used as IKK inhibitors. WO 2002051849 describes substituted benzothiophene compounds having hydrazine moieties that are used as cyclin dependent kinase 4 inhibitors. WO 03/037886 reports heteroaromatic carboxamide derivatives for the treatment of inflammation.

The work cited above supports the principle that inhibition of IKK will be beneficial in the treatment of various disease states. Some protein therapeutics are in late development or have been approved for use in particular diseases. Protein therapeutics are costly to produce and have bioavailability and stability problems. Therefore a need exists for new small molecule inhibitors of IKK activity with optimized efficacy, pharmacokinetic and safety profiles.

All references cited in this application are incorporated herein in their entirety.

BRIEF SUMMARY OF THE INVENTION

It is therefore an object of this invention to provide novel compounds which inhibit IKK according to the following formula (I):

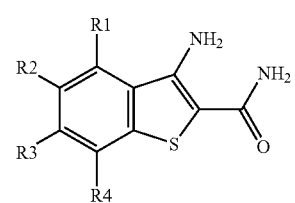

Formula (I)

wherein variables $R_1$, $R_2$, $R_3$, and $R_4$ are described herein. The work cited above supports the principle that inhibition of IKK activity will be beneficial in the treatment of various disease states.

It is therefore an object of the invention to provide compounds which inhibit IKK activity.

It is a further object of the invention to provide methods for treating diseases and pathological conditions involving inflammation such as chronic inflammatory disease, autoimmune disease and cancer using the novel compounds of the invention.

It is yet a further object of the invention to provide processes of preparation of the above-mentioned novel compounds.

DETAILED DESCRIPTION OF THE INVENTION

In a first broad generic embodiment of the invention, there are provided compounds of the formula (I):

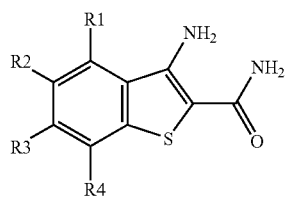

Formula (I)

wherein $R_1$ is:
a) hydrogen,
b) halogen,
c) $C_{1-8}$ alkyl, optionally partially or fully halogenated,
d) $C_{3-7}$ heterocycle or $C_{3-7}$ cycloalkyl, optionally substituted with one or two $R_8$,
e) $C_{1-8}$ alkoxy, optionally partially or fully halogenated and optionally substituted with $C_{3-7}$ cycloalkyl, phenyl, pyridyl, morpholine, —OH, —N($R_5$)($R_6$), —C(O)NR$_5$R$_6$ or $C_{1-6}$ alkoxy,
f) $C_{3-8}$ cycloalkoxy, optionally partially or fully halogenated and optionally substituted with $C_{3-7}$ cycloalkyl, phenyl, pyridyl, morpholine, —OH, —N($R_5$)($R_6$), —C(O)NR$_5$R$_6$ or $C_{1-6}$ alkoxy,
g) —N(R5)(R$_6$)
h) $C_{1-6}$alkylthio, optionally partially or fully halogenated,
i) aryl, optionally substituted with one or two $R_8$, or
j) heteroaryl selected from furanyl, thienyl, pyridyl, pyrrolyl, imidazolyl, triazolyl and benzofuranyl, optionally substituted with one or two $R_8$;

$R_2$ is
a) hydrogen,
b) halogen,
c) phenyl,
d) methoxy, or
e) methyl;

$R_3$ is
a) hydrogen,
b) halogen,
c) $C_{1-6}$alkyl, optionally partially or fully halogenated and optionally substituted with —N($R_5$)($R_6$);
d) $C_{1-6}$alkoxy, optionally partially or fully halogenated and optionally substituted with —N($R_5$)($R_6$);
e) —N($R_5$)($R_6$);
f) $C_{1-6}$alkylthio, optionally partially or fully halogenated and optionally substituted with —N($R_5$)($R_6$);
g) heterocyclyl selected from from 1-piperidinyl, 1-piperazinyl, 4-morpholinyl, 1-azepanyl, 1-pyrrolidinyl, 1,4-diazacycloheptan-1-yl, 1-azepanyl, 2,5-diazabicyclo[2.2.1]heptan-2-yl, oxazepan-4-yl and 4-thiomorpholino, optionally independently substituted with one to three $R_7$,
h) aryl, optionally substituted with one or two $R_8$, or
i) heteroaryl selected from furanyl, thienyl, pyridyl, pyrrolyl, imidazolyl, and benzofuranyl, optionally substituted with one or two $R_8$;

$R_4$ is
a) hydrogen,
b) halogen,
c) heteroaryl selected from furyl, imidazolyl, pyridyl or thienyl,
d) phenyl, optionally substituted with cyano, $C_{1-6}$alkoxy, hydroxyC$_{1-6}$alkyl, aminoC$_{1-6}$alkyl, halogen or phenyl,
e) $C_{1-6}$ alkyl, optionally partially or fully halogenated and optionally substituted with —NH$_2$, —OH, or —C(O)NH$_2$,
f) —C(O)NR$_5$R$_6$,
g) $C_{1-6}$ alkoxy, optionally partially or fully halogenated and optionally substituted with —OH, —N($R_5$)($R_6$), or $C_{1-8}$ alkoxy,
h) cyano, or
i) —N($R_5$)($R_6$);

$R_5$ and $R_6$ are independently selected from
H, $C_{1-6}$alkyl, —C(O)C$_{1-6}$alkyl, —SO$_2$C$_{1-6}$alkyl, —S(O)$_2$phenyl, pyridyl, benzyl, piperidinyl, phenylethyl, —C(O)morpholin-4-yl, —C(O)NH$_2$, —C(NH)NH$_2$ or —C(O)OMe;

$R_7$ is
—OH, —CN, oxo, —C(O)NH$_2$, —NH$_2$, —NHC$_{1-3}$alkyl, —CH$_2$NH$_2$, —CH$_3$, —NHC(O)NH$_2$, —NHC(NH)NH$_2$, —NHC(O)morpholin-4-yl, —NHSO$_2$C$_{1-3}$alkyl, —NHC(O)NH$_2$, —NHC(O)OC$_{1-3}$alkyl, $C_{1-6}$alkoxy, H$_2$NCH(R$_{10}$)C(O)—, HOCH(R$_9$)CH$_2$NH—, R$_9$CH$_2$CH(OH)CH$_2$NH— or R$_9$OCH$_2$CH(OH)CH$_2$NH—, or R$_7$ is 2-hydroxyethylamino, methylcarbamimidoyl, methanesulfonylamino, methylsulfonylhydrazino, 2-hydroxypropylamino, 2,3-dihydroxypropylamino, carbamoylmethylamino or N'-phenylhydrazinocarbonyl, —NHCH$_2$CO$_2$H;

$R_8$ is
$C_{1-6}$alkyl, $C_{1-6}$alkoxy, hydroxyC$_{1-6}$alkyl, halogen, —CN, —CO$_2$H, —CO$_2$C$_{1-6}$alkyl, —S(O)$_2$C$_{1-6}$alkyl, SC$_{1-6}$alkyl, —NO$_2$, —OH, —CF$_3$, —N($R_5$)($R_6$), —NHC(O)NHC$_{1-6}$alkyl, —C(O)N($R_5$)($R_6$) or phenyl or pyridyl, optionally substituted with halogen, $C_{1-6}$alkyl, —CN or $C_{1-6}$alkoxy;

$R_9$ is
$C_{1-6}$alkyl, an aryl or a heteroaryl group selected from phenyl, naphthly, imidazolyl, thienyl, thiazolyl, pyridyl, pyrimidyl, pyrazinyl, benzothiophenyl, benzothiazolyl, indolyl, benzimidazoyl, quinolinyl, isoquinolinyl, benzo[1,3]dioxoly, 2,3-dihydro-benzo[1,4]dioxinyl, 1-oxo-1,3-dihydro-isobenzofuranyl, 2,3-dihydro-benzofuranyl, 3-oxo-3,4-dihydro-2H-benzo[1,4]oxazinyl and 2-oxo-2,3-dihydro-benzooxazoly, and wherein $R_9$ is optionally substituted with one to three $R_{11}$ $R_{10}$ is
$C_{1-6}$alkyl, —(CH$_2$)$_{1-4}$NH$_2$, phenyl or benzyl;

$R_{11}$ is
halogen, hydroxyl, $C_{1-6}$alkyl, benzyl, $C_{1-6}$alkoxy, phenoxy, phenylamino, hydroxyC$_{1-6}$alkyl, —CN, —CO$_2$H, —CO$_2$C$_{1-6}$alkyl, —N($R_5$)($R_6$), $C_{1-6}$alkylN($R_5$)($R_6$), —C(O)N($R_5$)($R_6$), —NO$_2$, —S(O)$_n$C$_{1-6}$alkyl and —S(O)$_n$N($R_5$)($R_6$), morpholinyl, or an aryl or a heteroaryl group selected from phenyl, imidazolyl, pyrazolyl, thienyl, oxazoly, thiazolyl, pyridyl, pyrimidyl, pyrazinyl, and benzo[1,3]dioxoly, and wherein $R_{11}$ is optionally substituted with one to three $R_{12}$; and $R_{12}$ is
halogen, hydroxyl, $C_{1-6}$alkyl, $C_{1-6}$alkoxy, —CN, —CO$_2$H, —CO$_2$C$_{1-6}$alkyl, —N($R_5$)($R_6$) and C(O)N($R_5$)($R_6$);

or the pharmaceutically acceptable salts, acids, esters or isomers thereof.

In a second embodiment of the invention there are provided compounds of formula (I) as described in the first embodiment immediately above and wherein:

$R_9$ is a phenyl, naphthalene-2-yl, naphthalene-1-yl or 2-thienyl, pyridyl or imidazoyly group optionally substituted with one or two groups selected from Cl, F, —$CH_3$, —CN, —$CO_2CH_3$, —C(O)$NR_5R_6$, —$NO_2$, —OH, —$NH_2$, —$CF_3$ and —$CH_3$;

In a third embodiment of the invention there are provided compounds of the formula (I) as described in the first embodiment immediately above and wherein:

$R_1$ is:
  a) $C_{1-3}$ alkyl, optionally partially or fully halogenated,
  b) $C_{1-4}$ alkoxy, optionally partially or fully halogenated and optionally substituted with $C_{3-7}$ cycloalkyl, phenyl, pyridyl, morpholine, —OH, —N($R_5$)($R_6$), —C(O)$NR_5R_6$ or $C_{1-6}$ alkoxy,
  c) $C_{3-8}$ cycloalkoxy, optionally partially or fully halogenated and optionally substituted with $C_{3-7}$ cycloalkyl, phenyl, pyridyl, morpholine, —OH, —N($R_5$)($R_6$), —C(O)$NR_5R_6$ or $C_{1-6}$ alkoxy,
  d) —$SCH_3$, or
  e) triazolyl, optionally substituted with one or two $R_8$;

$R_2$ is hydrogen;

$R_3$ is
  a) hydrogen,
  b) —$CH_2CH_2NH_2$, or
  c) heterocyclyl selected from from 1-piperidinyl, 1-piperazinyl, 4-morpholinyl, 1-azepanyl, 1-pyrrolidinyl, 1,4-diazacycloheptan-1-yl, 1-azepanyl, 2,5-diazabicyclo[2.2.1]heptan-2-yl, oxazepan-4-yl and 4-thiomorpholino, optionally substituted with one to three $R_7$, $R_4$ is
  a) hydrogen, or
  b) C(O)$NH_2$;

$R_5$ and $R_6$ are independently selected from H, $C_{1-2}$alkyl, —C(O)$CH_3$, —$SO_2CH_3$ or benzyl;

$R_7$ is
  —OH, —CN, oxo, —C(O)$NH_2$, —$NH_2$, —NH$C_{1-3}$alkyl, —$CH_2NH_2$, —$CH_3$, —NHC(O)$NH_2$, —NHC(NH)$NH_2$, —NHC(O)morpholin-4-yl, —NHSO$_2C_{1-3}$alkyl, —NHC(O)$NH_2$, —NHC(O)O$C_{1-3}$alkyl, $C_{1-6}$alkoxy, $H_2$NCH($R_{10}$)C(O)—, HOCH($R_9$)$CH_2$NH—, $R_9CH_2$CH(OH)$CH_2$NH— and $R_9$OCH$_2$CH(OH)$CH_2$NH—, or $R_7$ is 2-hydroxyethylamino, methylcarbamimidoyl, methanesulfonylamino, methylsulfonylhydrazino, 2-hydroxypropylamino, 2,3-dihydroxypropylamino, carbamoylmethylamino or N'-phenylhydrazinocarbonyl;

$R_8$ is
  $C_{1-6}$alkyl, $C_{1-6}$alkoxy, hydroxy$C_{1-6}$alkyl, halogen, —CN, —$CO_2H$, —$CO_2C_{1-6}$alkyl, —S(O)$_2C_{1-6}$alkyl, S$C_{1-6}$alkyl, —$NO_2$, —OH, —$CF_3$, —N($R_5$)($R_6$), —NHC(O)NH$C_{1-6}$alkyl, —C(O)N($R_5$)($R_6$) or phenyl or pyridyl, optionally substituted with halogen, $C_{1-6}$alkyl, —CN or $C_{1-6}$alkoxy;

$R_9$ is
  a phenyl, naphthalene-2-yl, naphthalene-1-yl, 2-thienyl or pyridyl group, optionally substituted with one or two groups selected from Cl, F, —$CH_3$, —CN, —$CO_2CH_3$, —C(O)$NR_5R_6$, —$NO_2$, —OH, —$NH_2$, —$CF_3$ and —$CH_3$;

$R_{10}$ is $C_{1-6}$alkyl, —(CH$_2$)$_{1-4}$NH$_2$, phenyl or benzyl;

or the pharmaceutically acceptable salts, acids, esters or isomers thereof with the provisos that at least one of $R_3$ or $R_4$ is not hydrogen.

In a fourth embodiment of the invention there are provided compounds of the formula (I) as described in the embodiment immediately above and wherein:

$R_1$ is:
  a) $C_{1-3}$ alkyl,
  b) —$CF_3$,
  c) $C_{1-4}$ alkoxy, optionally partially or fully halogenated and optionally substituted with $C_{3-7}$ cycloalkyl, phenyl, pyridyl, morpholine, —OH, —N($R_5$)($R_6$), —C(O)$NR_5R_6$ or $C_{1-6}$ alkoxy,
  d) $C_{3-6}$ cycloalkoxy,
  e) —$SCH_3$, or
  f) triazolyl, optionally substituted with one or two $R_8$;

$R_2$ is hydrogen $R_3$ is
  a) heterocyclyl selected from from 1-piperidinyl, 1-piperazinyl, 1-azepanyl, 1,4-diazacycloheptan-1-yl and 1-azepanyl, and is optionally substituted with one to three $R_7$, or
  b) —$CH_2CH_2$ $NH_2$;

$R_4$ is hydrogen;

$R_5$ and $R_6$ are independently selected from H, $C_{1-2}$alkyl, —C(O)$CH_3$, —$SO_2CH_3$ and benzyl;

$R_7$ is
  —OH, —CN, oxo, —C(O)$NH_2$, —$NH_2$, —NH$C_{1-3}$alkyl, —$CH_2NH_2$, —$CH_3$, —NHC(O)$NH_2$, —NHC(NH)$NH_2$, —NHC(O)morpholin-4-yl, —NHSO$_2C_{1-3}$alkyl, —NHC(O)$NH_2$, —NHC(O)O$C_{1-3}$alkyl, $C_{1-6}$alkoxy, $H_2$NCH($R_{10}$)C(O)—, HOCH($R_9$)$CH_2$NH—, $R_9CH_2$CH(OH)$CH_2$NH— and $R_9$OCH$_2$CH(OH)$CH_2$NH—, or $R_7$ is 2-hydroxyethylamino, methylcarbamimidoyl, methanesulfonylamino, methylsulfonylhydrazino, 2-hydroxypropylamino, 2,3-dihydroxypropylamino, carbamoylmethylamino or N'-phenylhydrazinocarbonyl;

$R_8$ is
  $C_{1-2}$alkyl, —OCH$_3$, —CH$_2$OH, halogen, —CN, —$CO_2H$, —$CO_2C_{1-6}$alkyl, —S(O)$_2CH_3$, SCH$_3$, —$NO_2$, —OH, —$CF_3$, —N($R_5$)($R_6$), —NHC(O)NHCH$_3$, —C(O)N($R_5$)($R_6$) or phenyl or pyridyl, optionally substituted with halogen, $C_{1-6}$alkyl, —CN or $C_{1-6}$alkoxy;

$R_9$ is
  a phenyl group, optionally substituted with one or two groups selected from Cl, F, —$CH_3$, —CN, —$CO_2CH_3$, —C(O)$NR_5R_6$, —$NO_2$, —OH, —$NH_2$, —$CF_3$ and —$CH_3$, or $R_9$ is naphthalene-2-yl, naphthalene-1-yl or 2-thienyl;

$R_{10}$ is $C_{1-6}$alkyl, —(CH$_2$)$_{1-4}$NH$_2$, phenyl or benzyl;

or the pharmaceutically acceptable salts, acids, esters or isomers thereof.

In a fifth embodiment of the invention there are provided compounds of the formula (I) as described in the second embodiment wherein:

$R_1$ is:
  a) $C_{1-3}$ alkyl,
  b) —$CF_3$,
  c) $C_{1-4}$ alkoxy, optionally partially or fully halogenated and optionally substituted with $C_{3-7}$ cycloalkyl, phenyl, pyridyl, morpholine, —OH, —N($R_5$)($R_6$), —C(O)$NR_5R_6$ or $C_{1-6}$ alkoxy,
  d) $C_{3-8}$ cycloalkoxy, or
  e) —$SCH_3$;

$R_2$ is hydrogen;

$R_3$ is
  a) hydrogen, or
  b) $CH_2CH_2NH_2$;

$R_4$ is $C(O)NH_2$;

$R_5$ and $R_6$ are independently selected from

H, $C_{1-2}$alkyl, $—C(O)CH_3$, $—SO_2CH_3$ or benzyl;

or the pharmaceutically acceptable salts, acids, esters or isomers thereof.

In still another embodiment, there are provided the following compounds:

TABLE I

| Structure | Name |
|---|---|
| 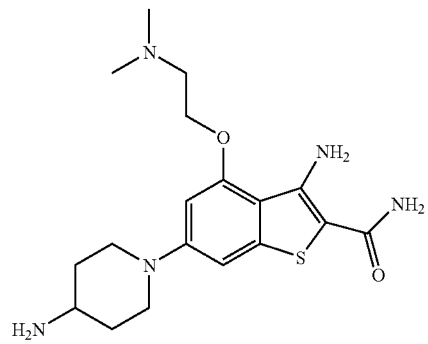 | 3-Amino-6-(4-amino-piperidin-1-yl)-4-(2-dimethylamino-ethoxy)-benzo[b]thiophene-2-carboxylic acid amide |
| 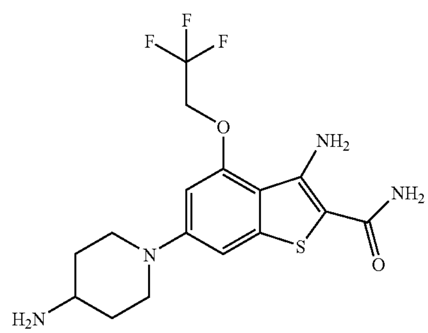 | 3-Amino-6-(4-amino-piperidin-1-yl)-4-(2,2,2-trifluoro-ethoxy)-benzo[b]thiophene-2-carboxylic acid amide |
| 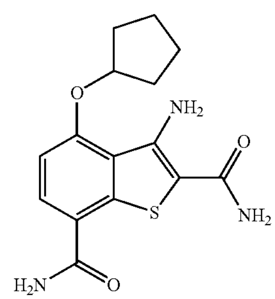 | 3-Amino-4-cyclopentyloxy-benzo[b]thiophene-2,7-dicarboxylic acid diamide |
| 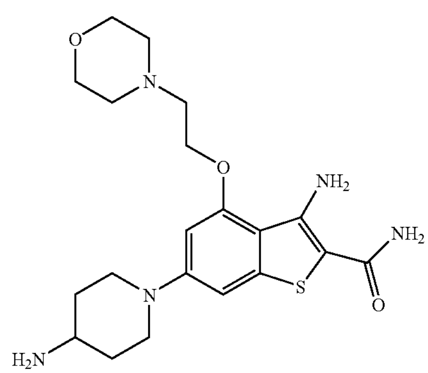 | 3-Amino-6-(4-amino-piperidin-1-yl)-4-(2-morpholin-4-yl-ethoxy)-benzo[b]thiophene-2-carboxylic acid amide |

TABLE I-continued

| Structure | Name |
|---|---|
| 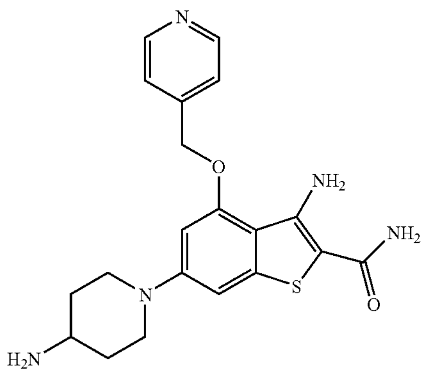 | 3-Amino-6-(4-amino-piperidin-1-yl)-4-(pyridin-4-ylmethoxy)-benzo[b]thiophene-2-carboxylic acid amide |
| 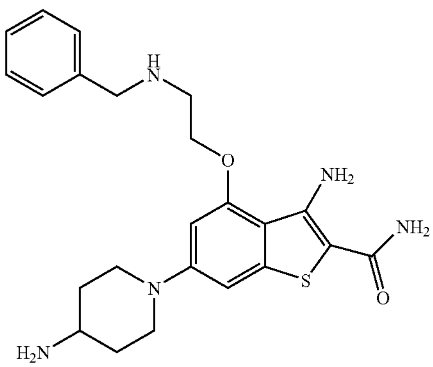 | 3-Amino-6-(4-amino-piperidin-1-yl)-4-(2-benzylamino-ethoxy)-benzo[b]thiophene-2-carboxylic acid amide |
| 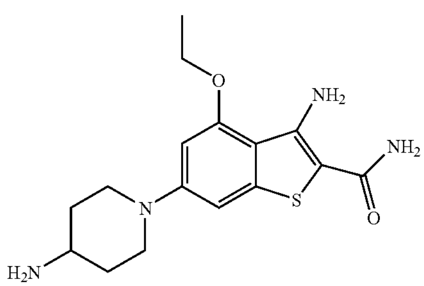 | 3-Amino-6-(4-amino-piperidin-1-yl)-4-ethoxy-benzo[b]thiophene-2-carboxylic acid amide |
| 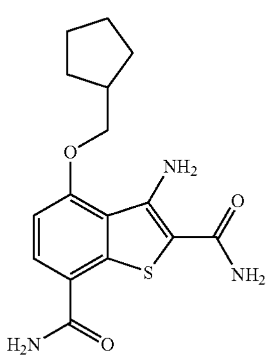 | 3-Amino-4-cyclopentylmethoxy-benzo[b]thiophene-2,7-dicarboxylic acid diamide |

TABLE I-continued

| Structure | Name |
|---|---|
| 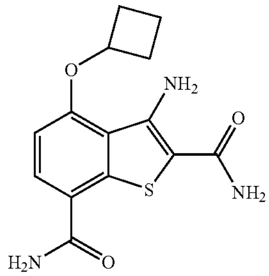 | 3-Amino-4-cyclobutoxy-benzo[b]thiophene-2,7-dicarboxylic acid diamide |
| 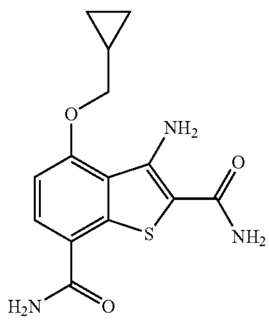 | 3-Amino-4-cyclopropylmethoxy-benzo[b]thiophene-2,7-dicarboxylic acid diamide |
| 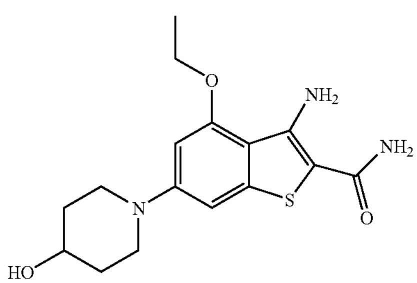 | 3-Amino-4-ethoxy-6-(4-hydroxy-piperidin-1-yl)-benzo[b]thiophene-2-carboxylic acid amide |
| 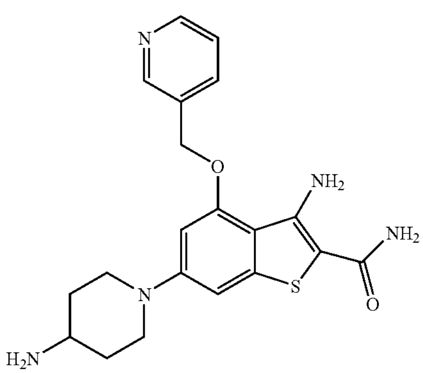 | 3-Amino-6-(4-amino-piperidin-1-yl)-4-(pyridin-3-ylmethoxy)-benzo[b]thiophene-2-carboxylic acid amide |
| 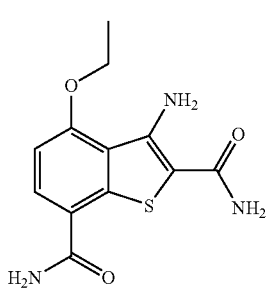 | 3-Amino-4-ethoxy-benzo[b]thiophene-2,7-dicarboxylic acid diamide |

TABLE I-continued

| Structure | Name |
|---|---|
| 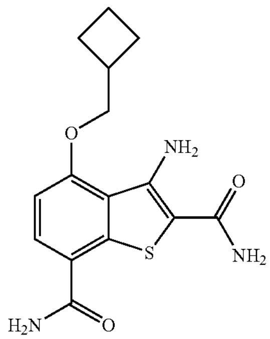 | 3-Amino-4-cyclobutylmethoxy-benzo[b]thiophene-2,7-dicarboxylic acid diamide |
| 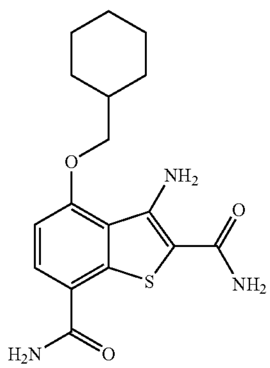 | 3-Amino-4-cyclohexylmethoxy-benzo[b]thiophene-2,7-dicarboxylic acid diamide |
| 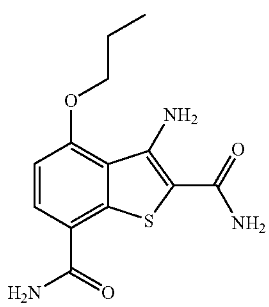 | 3-Amino-4-propoxy-benzo[b]thiophene-2,7-dicarboxylic acid diamide |
| 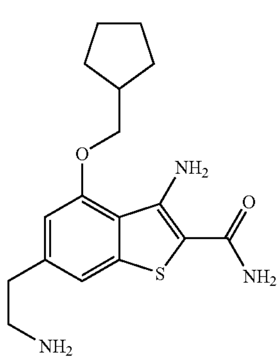 | 3-Amino-6-(2-amino-ethyl)-4-cyclopentylmethoxy-benzo[b]thiophene-2-carboxylic acid amide |

TABLE I-continued

| Structure | Name |
|---|---|
| 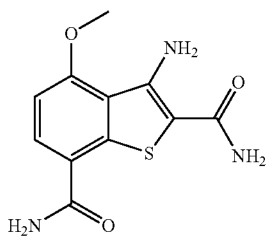 | 3-Amino-4-methoxy-benzo[b]thiophene-2,7-dicarboxylic acid diamide |
| 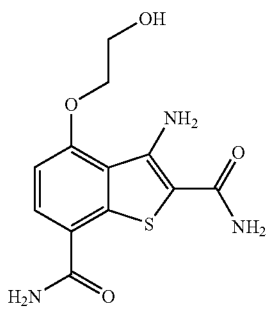 | 3-Amino-4-(2-hydroxy-ethoxy)-benzo[b]thiophene-2,7-dicarboxylic acid diamide |
| 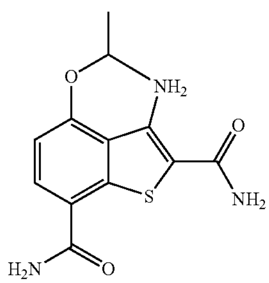 | 3-Amino-4-isopropoxy-benzo[b]thiophene-2,7-dicarboxylic acid diamide |
| 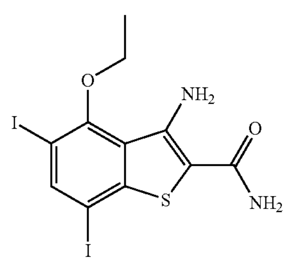 | 3-Amino-4-ethoxy-5,7-diiodo-benzo[b]thiophene-2-carboxylic acid amide |
| 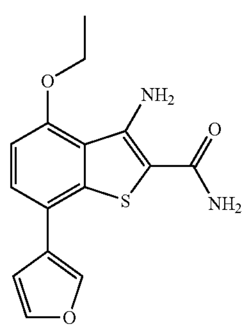 | 3-Amino-4-ethoxy-7-furan-3-yl-benzo[b]thiophene-2-carboxylic acid amide |

TABLE I-continued

| Structure | Name |
|---|---|
| 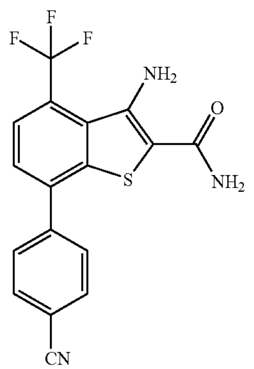 | 3-Amino-7-(4-cyano-phenyl)-4-trifluoromethyl-benzo[b]thiophene-2-carboxylic acid amide |
| 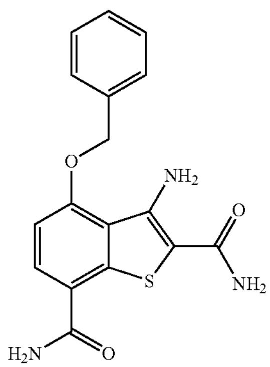 | 3-Amino-4-benzyloxy-benzo[b]thiophene-2,7-dicarboxylic acid diamide |
| 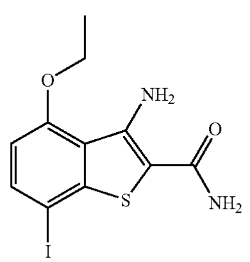 | 3-Amino-4-ethoxy-7-iodo-benzo[b]thiophene-2-carboxylic acid amide |
| 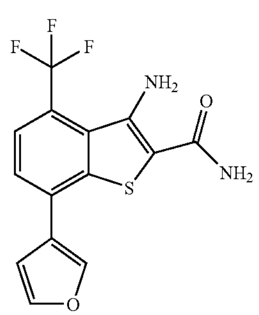 | 3-Amino-7-furan-3-yl-4-trifluoromethyl-benzo[b]thiophene-2-carboxylic acid amide |

TABLE I-continued

| Structure | Name |
|---|---|
|  | 3-Amino-4-cyclopentylmethoxy-6-[2-(di-aminomethyl-amino)-ethyl]-benzo[b]thiophene-2-carboxylic acid amide |
| 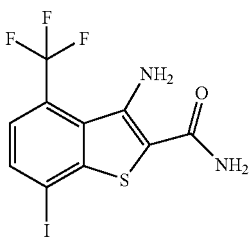 | 3-Amino-7-iodo-4-trifluoromethyl-benzo[b]thiophene-2-carboxylic acid amide |
| 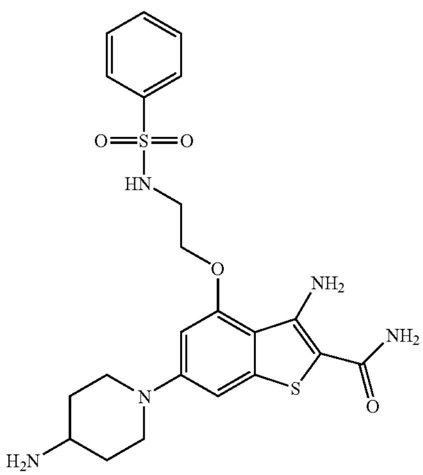 | 3-Amino-6-(4-amino-piperidin-1-yl)-4-(2-benzenesulfonylamino-ethoxy)-benzo[b]thiophene-2-carboxylic acid amide |
| 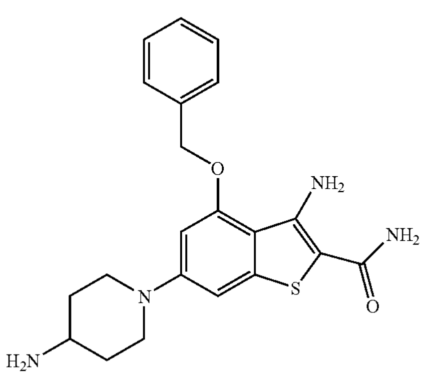 | 3-Amino-6-(4-amino-piperidin-1-yl)-4-benzyloxy-benzo[b]thiophene-2-carboxylic acid amide |

TABLE I-continued

| Structure | Name |
|---|---|
| 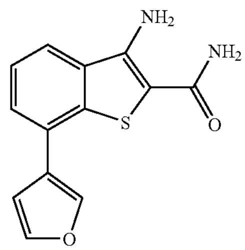 | 3-Amino-7-furan-3-yl-benzo[b]thiophene-2-carboxylic acid amide |
| 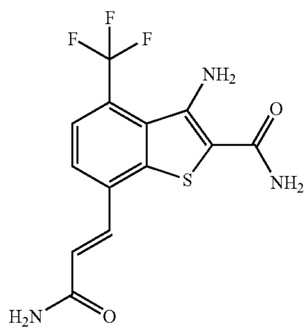 | 3-Amino-7-((Z)-2-carbamoyl-vinyl)-4-trifluoromethyl-benzo[b]thiophene-2-carboxylic acid amide |
| 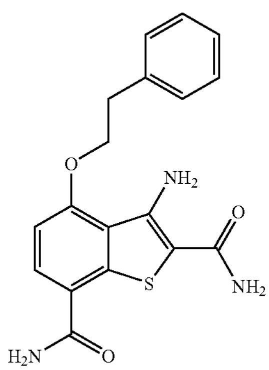 | 3-Amino-4-phenethyloxy-benzo[b]thiophene-2,7-dicarboxylic acid diamide |
| 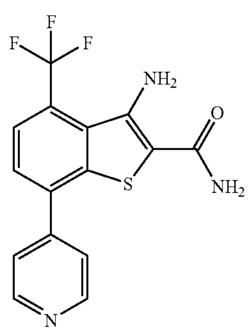 | 3-Amino-7-pyridin-4-yl-4-trifluoromethyl-benzo[b]thiophene-2-carboxylic acid amide |
| 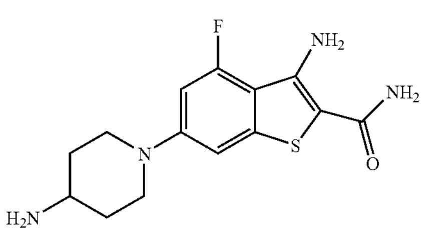 | 3-Amino-6-(4-amino-piperidin-1-yl)-4-fluoro-benzo[b]thiophene-2-carboxylic acid amide |

TABLE I-continued

| Structure | Name |
|---|---|
| 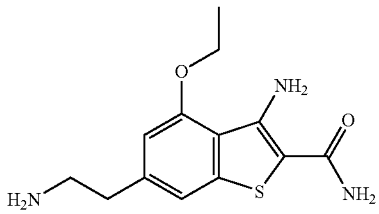 | 3-Amino-6-(2-amino-ethyl)-4-ethoxy-benzo[b]thiophene-2-carboxylic acid amide |
| 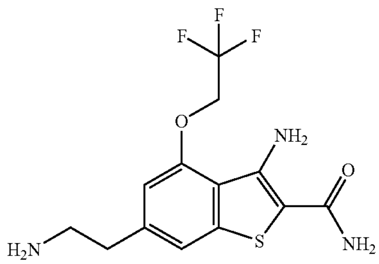 | 3-Amino-6-(2-amino-ethyl)-4-(2,2,2-trifluoro-ethoxy)-benzo[b]thiophene-2-carboxylic acid amide |
| 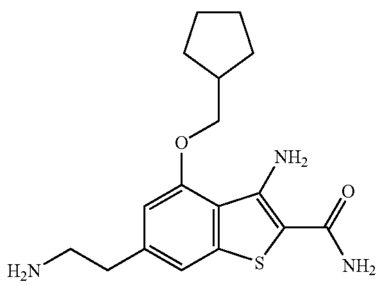 | 3-Amino-6-(2-amino-ethyl)-4-cyclopentyloxy-benzo[b]thiophene-2-carboxylic acid amide |
| 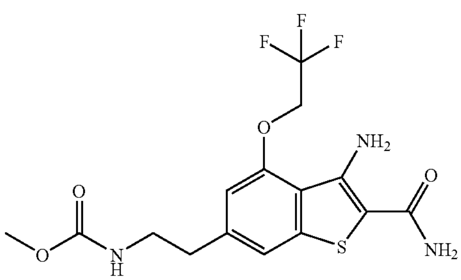 | {2-[3-Amino-2-carbamoyl-4-(2,2,2-trifluoro-ethoxy)-benzo[b]thiophen-6-yl]-ethyl}-carbamic acid methyl ester |
| 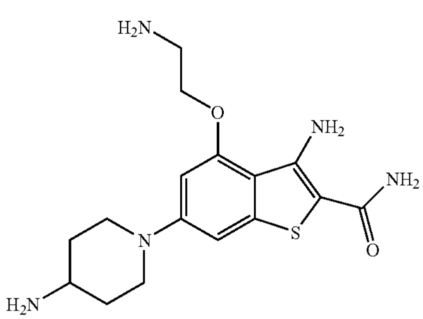 | 3-Amino-4-(2-amino-ethoxy)-6-(4-amino-piperidin-1-yl)-benzo[b]thiophene-2-carboxylic acid amide |

TABLE I-continued

| Structure | Name |
|---|---|
| (structure) | 4-(2-Acetylamino-ethoxy)-3-amino-6-(4-a-mino-piperidin-1-yl)-benzo[b]thiophene-2-carboxylic acid amide |
| (structure) | 3-Amino-6-(4-amino-piperidin-1-yl)-4-methylsulfanyl-benzo[b]thiophene-2-carboxylic acid amide |

In a further embodiment, there are provided the following compounds:
3-Amino-6-(4-amino-piperidin-1-yl)-4-(2-dimethylamino-ethoxy)-benzo[b]thiophene-2-carboxylic acid amide;
3-Amino-6-(4-amino-piperidin-1-yl)-4-(2,2,2-trifluoro-ethoxy)-benzo[b]thiophene-2-carboxylic acid amide;
3-Amino-4-cyclopentyloxy-benzo[b]thiophene-2,7-dicarboxylic acid diamide;
3-Amino-6-(4-amino-piperidin-1-yl)-4-(2-morpholin-4-yl-ethoxy)-benzo[b]thiophene-2-carboxylic acid amide;
3-Amino-6-(4-amino-piperidin-1-yl)-4-(pyridin-4-ylmethtoxy)-benzo[b]thiophene-2-carboxylic acid amide;
3-Amino-6-(4-amino-piperidin-1-yl)-4-ethoxy-benzo[b]thiophene-2-carboxylic acid amide;
3-Amino-6-(4-amino-piperidin-1-yl)-4-(2-benzylamino-ethoxy)-benzo[b]thiophene-2-carboxylic acid amide;
3-Amino-4-cyclopentylmethoxy-benzo[b]thiophene-2,7-dicarboxylic acid diamide;
3-Amino-4-cyclobutoxy-benzo[b]thiophene-2,7-dicarboxylic acid diamide;
3-Amino-4-cyclopropylmethoxy-benzo[b]thiophene-2,7-dicarboxylic acid diamide;
3-Amino-6-(2-amino-ethyl)-4-ethoxy-benzo[b]thiophene-2-carboxylic acid amide;
3-Amino-6-(2-amino-ethyl)-4-ethoxy-benzo[b]thiophene-2-carboxylic acid amide;
3-Amino-6-(2-amino-ethyl)-4-(2,2,2-trifluoro-ethoxy)-benzo[b]thiophene-2-carboxylic acid amide;
3-Amino-6-(2-amino-ethyl)-4-cyclopentyloxy-benzo[b]thiophene-2-carboxylic acid amide;
3-Amino-4-(2-amino-ethoxy)-6-(4-amino-piperidin-1-yl)-benzo[b]thiophene-2-carboxylic acid amide;
4-(2-Acetylamino-ethoxy)-3-amino-6-(4-amino-piperidin-1-yl)-benzo[b]thiophene-2-carboxylic acid amide.

or the pharmaceutically acceptable salts, acids, esters or isomers thereof.

Another embodiment of the invention comprises a method of treating an inflammatory or autoimmune condition by administration of a therapeutically effective amount of compounds of formula I as defined in the first embodiment to a patient of need of such treatment.

In all the compounds disclosed hereinabove in this application, in the event the nomenclature is in conflict with the structure, it shall be understood that the compound is defined by the structure.

Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formula I can exist in more than one tautomeric form. The invention includes all such tautomers.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and N—($C_1$-$C_4$ alkyl)$_4^+$ salts.

In addition, the compounds of this invention include prodrugs of compounds of the formula (I). Prodrugs include those compounds that, upon simple transformation, are modified to produce the compounds of the invention. Simple chemical transformations include hydrolysis, oxidation and reduction which occur enzymatically, metabolically or otherwise. Specifically, when a prodrug of this invention is administered to a patient, the prodrug may be transformed into a compound of formula (I), thereby imparting the desired pharmacological effect.

The compounds of the invention are only those which are contemplated to be 'chemically stable' as will be appreciated by those skilled in the art. For example, a compound which would have a 'dangling valency', or a 'carbanion' are not compounds contemplated by the invention.

As used herein, the following abbreviations are used:
DMF is dimethylformamide;
DMSO is dimethyl sulfoxide
EtOAc is ethyl acetate;
EtOH is ethanol;
HPLC is high-performance liquid chromatography
MeOH is methanol;
THF is tetrahydrofuran;
TLC is thin layer chromatography All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, and butoxy. All alkyl, alkenyl and alkynyl groups shall be understood as being $C_{1-10}$ branched or unbranched where structurally possible and unless otherwise specified. Other more specific definitions are as follows:

The term "alkyl" refers to a saturated aliphatic radical containing from one to ten carbon atoms or a mono- or polyunsaturated aliphatic hydrocarbon radical containing from two to twelve carbon atoms unless otherwise stated. The mono- or polyunsaturated aliphatic hydrocarbon radical contains at least one double or triple bond, respectively. "Alkyl" refers to both branched and unbranched alkyl groups. Examples of "alkyl" include alkyl groups which are straight chain alkyl groups containing from one to eight carbon atoms and branched alkyl groups containing from three to ten carbon atoms. Other examples include lower alkyl groups which are straight chain alkyl groups containing from one to six carbon atoms and branched alkyl groups containing from three to six carbon atoms. It should be understood that any combination term using an "alk" or "alkyl" prefix refers to analogs according to the above definition of "alkyl". For example, terms such as "alkoxy", "alkythio" refer to alkyl groups linked to a second group via an oxygen or sulfur atom. "Alkanoyl" refers to an alkyl group linked to a carbonyl group (C=O). Each alkyl or alkyl analog described herein shall be understood to be optionally partially or fully halogenated.

The term "aroyl" as used in the present specification shall be understood to mean "benzoyl" or "naphthoyl".

The term "aryl" shall be understood to mean a 6-12 membered aromatic carbocycle, which can be a single ring or can be multiple rings fused together or linked covalently. The term "aryl" includes, for example, phenyl and naphthyl; other terms comprising "aryl" will have the same definition for the aryl component, examples of these moieties include: arylalkyl, aryloxy or arylthio.

The term "carbocycle" shall be understood to mean an aliphatic hydrocarbon radical containing from three to twelve carbon atoms. Carbocycles include hydrocarbon rings containing from three to ten carbon atoms. These carbocycles may be either aromatic or non-aromatic ring systems. The non-aromatic ring systems may be mono- or polyunsaturated. Preferred carbocycles unless otherwise specified include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl.

The term "halogen" refers to bromine, chlorine, fluorine or iodine.

The term "heterocycle" refers to a stable nonaromatic 4-8 membered (but preferably, 5 or 6 membered) monocyclic or nonaromatic 8-11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure. Preferred heterocycles include but are not limited to, for example pyrrolidinyl, tetrahydrofuranyl, tetrahydrothiophenyl, piperidinyl, piperazinyl, morpholinyl, tetrahydropyranyl, dioxanyl, oxazolinyl, thiazolinyl, imidazolinyl, tetrahydropyridinyl, homopiperidinyl, pyrrolinyl, tetrahydropyrimidinyl, decahydroquinolinyl, decahydroisoquinolinyl, thiomorpholinyl, thiazolidinyl.

The term "heteroaryl" shall be understood to mean an aromatic 5-8 membered monocyclic or 8-11 membered bicyclic ring containing 1-4 heteroatoms chosen from N, O and S. Included are the partially or fully saturated derivates thereof. Such heteroaryls unless otherwise specified include: pyridinyl, pyrimidinyl, pyrazinyl, pyridazinyl, pyrrolyl, imidazolyl, pyrazolyl, thienyl, furyl, isoxazolyl, thiazolyl, oxazolyl, triazolyl, tetrazolyl, isothiazolyl, quinolinyl, isoquinolinyl, indolyl, benzimidazolyl, benzofuranyl, benzoxazolyl, benzisoxazolyl, benzopyrazolyl, benzothiofuranyl, quinoxalinyl, quinazolinyl and indazolyl.

The term "heteroatom" as used herein shall be understood to mean atoms other than carbon such as O, N, S and P.

The terms "optional" or "optionally" mean that the subsequently described event or circumstances may or may not occur, and that the description includes instances where the event or circumstance occurs and instances in which it does not. For example, "optionally substituted aryl" means that the aryl radical may or may not be substituted and that the description includes both substituted aryl radicals and aryl radicals having no substitution.

The term "substituted" means that any one or more hydrogens on an atom of a group or moiety, whether specifically designated or not, is replaced with a selection from the indicated group of substituents, provided that the atom's normal valency is not exceeded and that the substitution results in a stable compound. If a bond to a substituent is shown to cross the bond connecting two atoms in a ring, then such substituent may be bonded to any atom on the ring. When a substituent is listed without indicating the atom via which such substituent is bonded to the rest of the compound, then such substituent may be bonded via any atom in such substituent. For example, when the substituent is piperazinyl, piperidinyl, or tetrazolyl, unless specified otherwise, such piperazinyl, piperidinyl, or tetrazolyl group may be bonded to the rest of the compound of the invention via any atom in such piperazinyl, piperidinyl, or tetrazolyl group. Generally, when any substituent or group occurs more than one time in any constituent or compound, its definition on each occurrence is independent of its definition at every other occurrence. Thus, for example, if a group is shown to be substituted with 0 to 2 R, then such group is optionally substituted with up to two R groups and R at each occurrence is selected independently from the defined list of possible R. Such combinations of substituents and/or variables, however, are permissible only if such combinations result in stable compounds.

In all alkyl groups or carbon chains where one or more carbon atoms are optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by oxo to result in definitions such as but not limited to: acyl, alkoxycarbonyl, alkylthiosulfone, alkylthiosulfonyl, amido etc.

Terms which are analogs of the above cyclic moieties such as aryloxy, heterocyclyloxy or heteroaryl amine shall be understood to mean an aryl, heteroaryl, heterocycle as defined above attached to it's respective group.

As used herein, "nitrogen" and "sulfur" include any oxidized form of nitrogen and sulfur and the quaternized form of any basic nitrogen. For example, if Y is —S—$C_{1-6}$ alkyl, unless otherwise specified, this shall be understood to include —S(O)—$C_{1-6}$ alkyl and —S(O)$_2$—$C_{1-6}$ alkyl.

Methods of Therapeutic Use

In accordance with the invention, there are provided novel methods of using the compounds of the formula (I). The compounds of the invention are effective in inhibiting the activity of IKKβ and/or IKKα. In particular, these compounds are useful in blocking disease processes exacerbated by IKKβ-mediated NF-κB activation and IKKα activation of B cell activity or the cell cycle regulatory gene Cyclin D1. In blocking NF-κB activation, compounds of the invention effectively block transcription of genes encoding inflammatory cytokines including IL-1, IL-2, IL-6, IL-8, TNFα, chemokines including IL-8 and RANTES as well as other pro-inflammatory molecules including COX-2 and cell adhesion molecules such as ICAM-1, VCAM-1 and E-selectin. These mediators play a key role in the etiology of inflammatory, autoimmune and cardiovascular disorders and cancer. Preventing the production of these mediators is a desirable means for treating these disorders. Thus there are provided methods for treating these conditions using the compounds of the invention. Such inflammatory and autoimmune conditions include but are not limited to osteoarthritis, reperfusion injury, asthma, chronic obstructive pulmonary disease (COPD), multiple sclerosis, Guillain-Barre syndrome, Crohn's disease, ulcerative colitis, psoriasis, graft versus host disease, systemic lupus erythematosus, rheumatoid arthritis, Alzheimer's disease, toxic shock syndrome, insulin-dependent diabetes mellitis, acute and chronic pain, thermal injury, adult respiratory distress syndrome (ARDS), multiple organ injury secondary to trauma, acute glomerulonephritis, dermatoses with acute inflammatory components, acute purulent meningitis or other central nervous system disorders, Grave's disease, myasthenia gravis, scleroderma and atopic dermatitis. Such cardiovascular disorders include but are not limited to atherosclerosis, myocardial infarction and stroke. Such cancers include but are not limited to lymphoid-, myeloid- and epithelial-derived malignancies including leukemia, lymphomas and breast, gastric, colorectal, lung, and pancreatic cancers. The compounds of the invention can also be used to treat other disorders associated with IKK activation of NF-κB unrelated to those listed above or discussed in the Background of the Invention. For example, the compounds of the invention may also be useful in the treatment of cancer by enhancing the effectiveness of chemotherapeutic agents. Therefore, the invention also provides methods of treating inflammatory and autoimmune diseases, and other diseases including cancer, comprising administering to a patient in need of such treatment a pharmaceutically effect amount of a compound according to the invention.

For therapeutic use, the compounds of the invention may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous. Compositions comprising the compounds of the invention for each of the aforementioned routes of administration will be apparent to the skilled artisan. The invention also provides for pharmaceutical compositions including a therapeutically effective amount of the compounds according to the invention. Such pharmaceutical compositions will include pharmaceutically acceptable carriers and adjuvants as further described below.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 15%, but more preferably at least about 20%, of a compound of the invention (w/w) or a combination thereof. Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements are well-recognized in the art and may be selected by those of ordinary skill in the art from available methods and techniques suitable for a particular patient. In some embodiments, dosage levels range from about 10-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

Synthetic Methods

The invention additionally provides for methods for making compounds of formula (I). Methods that may be used for synthesis of the compounds of the invention are also described in U.S. non-provisional Ser. No. 10/453,175 and are incorporated herein by reference.

The compounds of the invention may be prepared by the general methods and examples presented below, and methods known to those of ordinary skill in the art. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Reaction progress may be monitored by conventional methods such as thin layer chromatography (TLC). Intermediates and products may be purified by methods known in the art, including column chromatography, HPLC or recrystallization.

As illustrated in Scheme I, compounds of formula (I) may be prepared by reaction of an optionally substituted benzonitrile (II) with 2-thioacetamide in the presence of a suitable base such as potassium carbonate, in a suitable solvent such as DMF. Initially formed compounds of formula (I) may be further modified by methods known in the art to produce additional compounds of formula (I). Some of these methods are described in the Synthetic Examples section below.

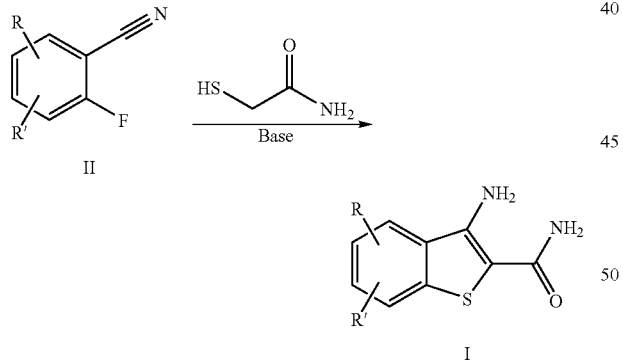

7-Substituted compounds of formula I may be prepared as illustrated in Scheme II.

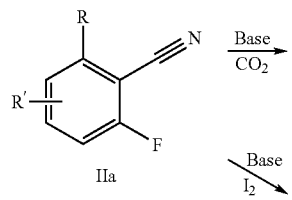

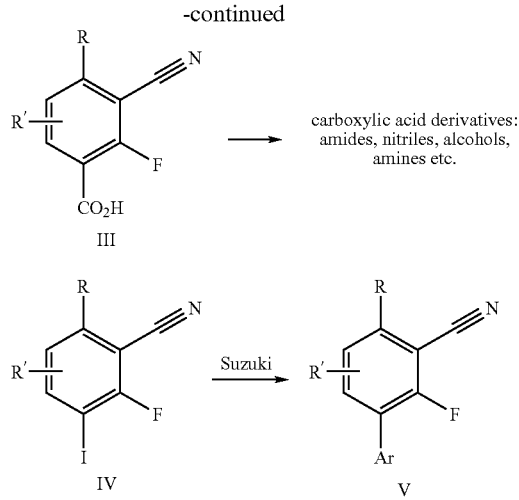

As illustrated in Scheme II, a 2-fluoro-6-substituted benzonitrile (IIa) is reacted with a strong base such as lithium diisopropylamide in a suitable solvent such as THF, preferably at about −78°. The resulting anion is reacted with $CO_2$, for example by pouring onto dry ice. Treatment with aqueous acid provides the benzoic acid intermediate III. This may then be converted into carboxylic acid derivatives such as amides, esters or nitriles by methods known in the art. Reduction of the carboxylic acid III, for example by treatment with diisobutylaluminum hydride provides the alcohol which may be further modified by methods known in the art. Conversion of the carboxylic acid III to an amine, for example by a Schmidt reaction provides the aniline derivative which may be further modified by methods known in the art to provide substituted amines or amides.

Treatment of IIa with a strong base such as n-BuLi in a suitable solvent such as THF, preferably at around −78° C., followed by reaction with iodine provides the iodo intermediate IV. Suzuki coupling with an aryl or heteroaryl boronic acid provides the desired 7-aryl or heteroaryl intermediate V. Alternatively, one may convert IV to the corresponding boronic acid derivative and perform the Suzuki coupling with an aryl or heteroaryl iodide.

Each of the above-mentioned intermediates (IIa, III and the corresponding carboxylic acid derivatives, IV or V) may be converted to a compound of formula (I) by the procedure described in Scheme I.

SYNTHETIC EXAMPLES

Example 1

Synthesis of 3-amino-4-fluoro-6-morpholin-4-yl-benzo[b]thiophene-2-carboxylic acid amide

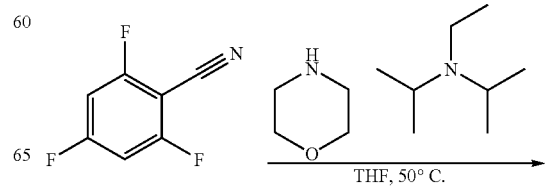

-continued

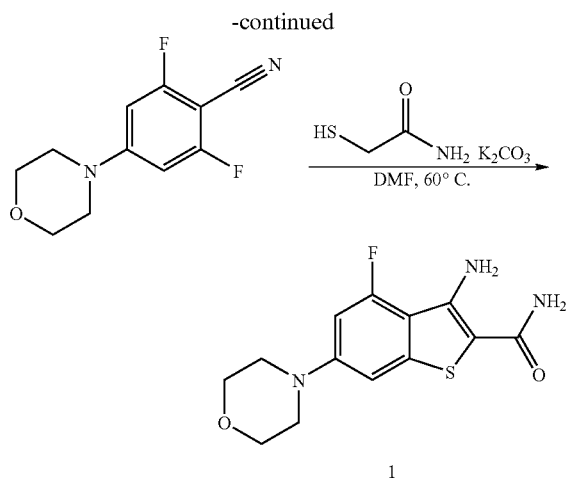

To a solution of 1.0 g (6.37 mmol) of 2,4,6-trifluorobenzonitrile in MeOH (25 mL) was added 0.6 mL (6.9 mmol) of morpholine and 1.2 mL (6.7 mmol) of N,N-diisopropylethylamine. The mixture was heated to 50° C. for 6 h then cooled to room temperature and diluted with $H_2O$ which caused a solid to precipitate from solution. The white solid was collected by filtration, washed with $H_2O$ and dried under vacuum to provide 0.98 g (68%) of 2,6-difluoro-4-morpholin-4-yl-benzonitrile as a white solid.

To a solution of 0.100 g (0.446 mmol) of 2,6-difluoro-4-morpholin-4-yl-benzonitrile in DMF (3 mL) was added 0.45 mL (0.50 mmol) of a 10% solution of 2-thioacetamide in MeOH along with 0.31 g (2.2 mmol) of potassium carbonate. The mixture was stirred at room temperature for 3 days. The mixture was diluted with $H_2O$ which caused a solid to precipitate from solution. The white solid was collected by filtration, washed with $H_2O$, and dried under vacuum to provide 0.10 g (76%) of the title compound as a white powder. MS calc. for $C_{13}H_{15}FN_3O_2S$ [M+H]$^+$: 296.34. Found: 296.23.

Example 2

Synthesis of 3-amino-4-methoxy-6-morpholin-4-yl-benzo[b]thiophene-2-carboxylic acid amide (2a) and 3-amino-4-ethoxy-6-morpholin-4-yl-benzo[b]thiophene-2-carboxylic acid amide (2b)

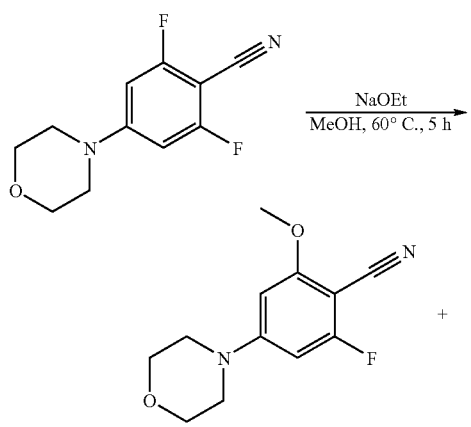

-continued

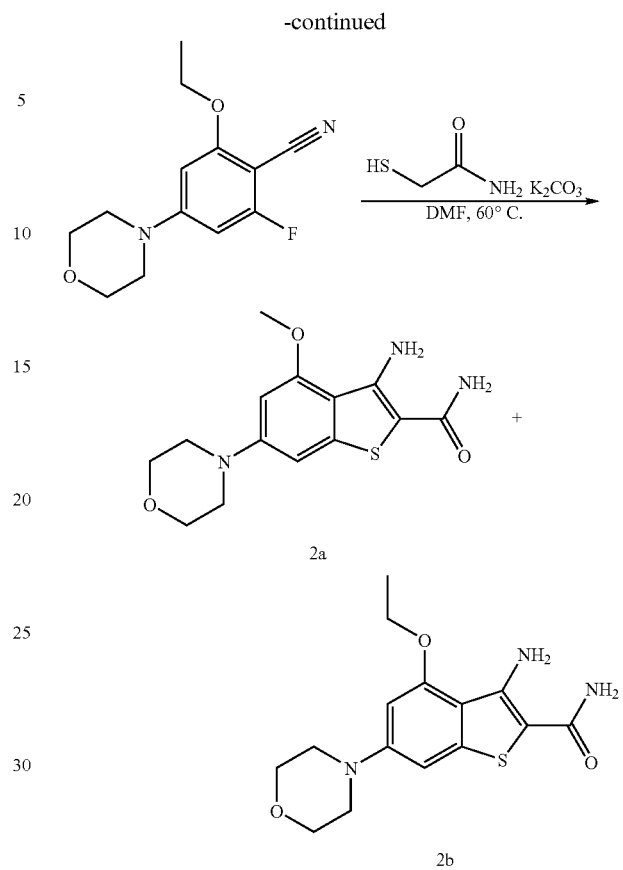

To a solution of 0.10 g (0.446 mmol) of 2,6-difluoro-4-morpholin-4-yl-benzonitrile in MeOH (5 mL), cooled to 0° C., was added 0.170 mL of a 21% wt solution of sodium ethoxide in EtOH. The mixture heated to 60° C. for 5 h. The mixture was cooled to room temperature and excess reactant was consumed by the addition of a saturated aqueous solution of $NH_4Cl$. The mixture was diluted with $H_2O$ and washed with EtOAc. The combined organic phase was washed with brine, dried over anhydrous $Na_2SO_4$ and concentrated under reduced pressure. The crude residue was purified by flash silica gel chromatography to provide 0.050 g (45%) of a white foam which consisted of a 1:2 mixture of 2-fluoro-6-methoxy-4-morpholin-4-yl benzonitrile and 2-fluoro-6-ethoxy-4-morpholin-4-yl benzonitrile.

To a solution of 0.050 g of the above mixture in DMF (2 mL) was added 0.27 mL (0.30 mmol) of a 10% solution of 2-thioacetamide in MeOH along with 0.15 g (1.1 mmol) of potassium carbonate. The mixture was heated at 60° C. for 24 h then cooled to room temperature and diluted with $H_2O$. The mixture was washed with $CH_2Cl_2$ and the combined organic phase was dried over anhydrous $Na_2SO_4$ and concentrated under reduced pressure. The crude residue was purified by flash silica gel chromatography using a 0-50% gradient of A (10% MeOH in $CH_2Cl_2$) to B ($CH_2Cl_2$) to provide a mixture of the title compounds. The products were separated using preparatory reverse phase HPLC to provide 0.009 g (28%) of 2a and 0.010 g (29%) of 2b as white powders. MS calc. for 2a $C_{14}H_{18}N_3O_3S$ [M+H]$^+$: 308.37. Found: 308.29. MS calc. for 2b $C_{15}H_{20}N_3O_3S$ [M+H]$^+$: 322.40. Found: 322.30.

Example 3

Synthesis of 3-amino-6-(4-amino-piperidin-1-yl)-4-fluoro-benzo[b]thiophene-2-carboxylic acid amide

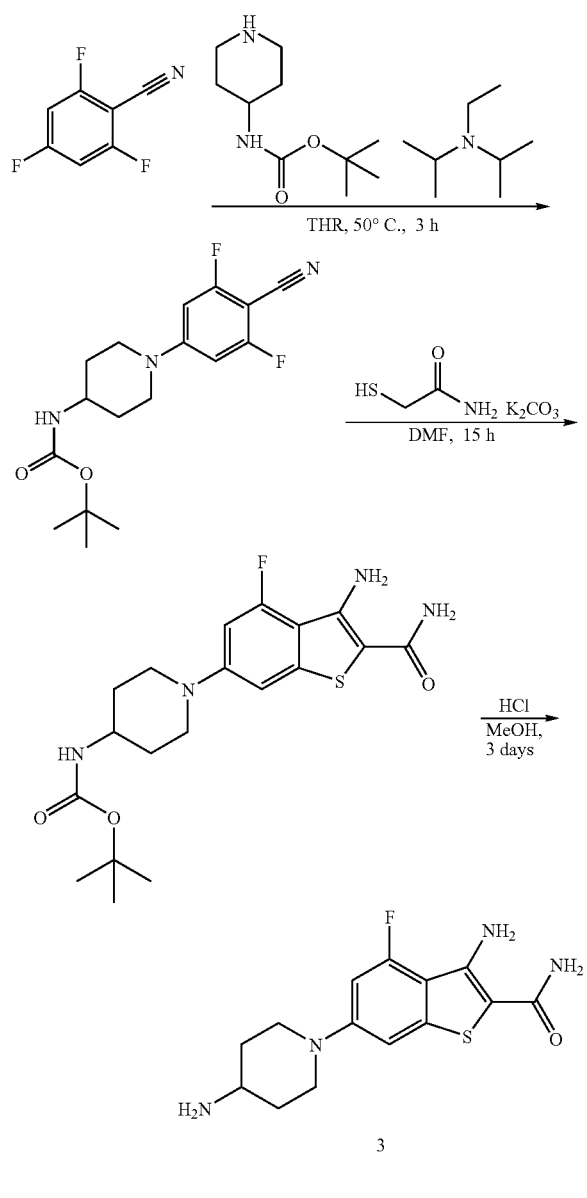

To a solution of 1.0 g (6.4 mmol) of 2,4,6-trifluorobenzonitrile in MeOH (25 mL) was added 1.3 g (6.5 mmol) of 4-N-boc-amino-piperidine along with 1.2 mL (6.7 mmol) of N,N-diisopropylethylamine. The mixture was stirred at room temperature for 3 days then concentrated under reduced pressure to provide a white solid. The solid was washed with large amounts of H$_2$O and dried under vacuum. The solid was recrystallized from hexane/EtOAc to provide 1.23 g (56%) of [1-(4-cyano-3,5-difluoro-phenyl)-piperidin-4-yl]-carbamic acid tert-butyl ester as a white solid.

To a solution of 0.10 g (0.30 mmol) of the above ester in DMF (3 mL) was added 0.30 mL (0.33 mmol) of a 10% solution of 2-thioacetamide in MeOH along with 0.20 g (1.4 mmol) of potassium carbonate. The mixture was stirred at room temperature for 15 h then diluted with H$_2$O and washed with CH$_2$Cl$_2$. The combined organic phase was dried over anhydrous Na$_2$SO$_4$ and concentrated under reduced pressure. The crude residue was purified by flash silica gel chromatography to provide 0.055 g (45%) of [1-(3-amino-2-carbamoyl-4-fluoro-benzo[b]thiophen-6-yl)-piperidin-4-yl]-carbamic acid tert-butyl ester as a clear oil.

To a solution of 0.055 g (0.14 mmol) of [1-(3-amino-2-carbamoyl-4-fluoro-benzo[b]thiophen-6-yl)-piperidin-4-yl]-carbamic acid tert-butyl ester in CH$_2$Cl$_2$ (1 mL) was added 0.07 mL (0.3 mmol) of a 4.0 M solution of HCl in 1,4-dioxane. The mixture was stirred at room temperature for 3 days during which time a solid precipitated from solution. The solid was collected by filtration and washed with CH$_2$Cl$_2$. The material was purified by reverse phase HPLC to provide 0.010 g (18%) of the title compound as a white solid. MS calc. for C$_{14}$H$_{17}$FN$_4$OS [M+H]$^+$: 309.38. Found: 309.26.

Example 4

Synthesis of 3-amino-6-(4-amino-piperidin-1-yl)-4-ethoxy-benzo[b]thiophene-2-carboxylic acid amide

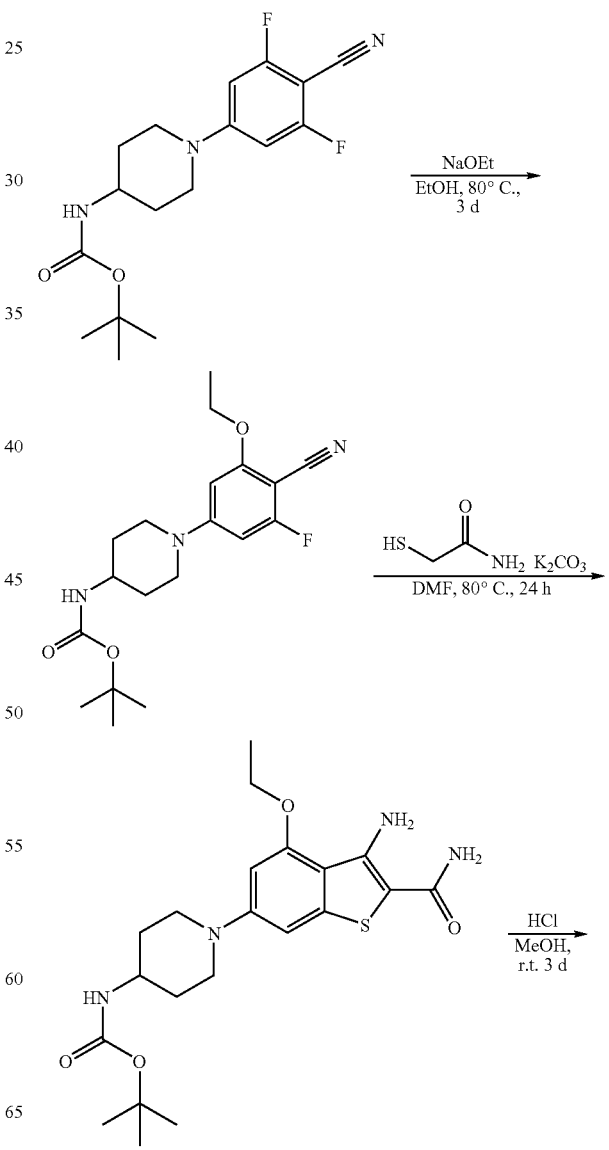

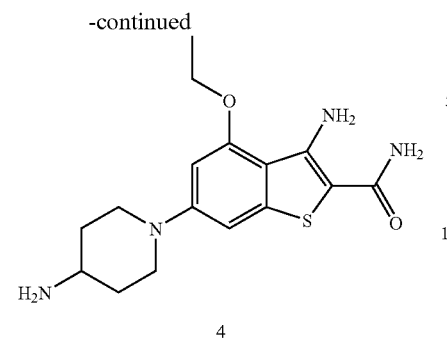

4

To a solution of 0.50 g (1.5 mmol) of [1-(4-cyano-3,5-difluoro-phenyl)-piperidin-4-yl]-carbamic acid tert-butyl ester in EtOH (15 mL), cooled to 0° C., was added 0.49 mL (1.5 mmol) of sodium ethoxide as a 21% wt. solution in EtOH. The mixture was heated to 80° C. for 3 days then cooled to room temperature and concentrated under reduced pressure. The residue was suspended in H$_2$O which caused a solid to precipitate from solution. The solid was collected by filtration and washed with H$_2$O and dried under vacuum. The solid was purified by recrysallization from EtOAc:hexanes to provide 0.311 g (58%) of 3-amino-6-(4-amino-piperidin-1-yl)-4-ethoxy-benzo[b]thiophene-2-carboxylic acid amide as a white solid.

To a solution of 0.311 g (0.856 mmol) of the above amide in DMF (5 mL) was added 0.91 mL (1.0 mmol) of a 10% solution of 2-thioacetamide in MeOH along with 0.70 g (5.1 mmol) of potassium carbonate. The mixture was heated to 80° C. for 24 h then cooled to room temperature and diluted with H$_2$O. The mixture was washed with CH$_2$Cl$_2$ and the combined organic phase was washed with H$_2$O, dried over anhydrous Na$_2$SO$_4$ and concentrated under reduced pressure. The residue was purified by flash silica gel chromatography to provide 0.093 g (25%) of [1-(3-amino-2-carbamoyl-4-ethoxy-benzo[b]thiophen-6-yl)-piperidin-4-yl]-carbamic acid tert-butyl ester as a white powder.

To a solution of 0.093 g (0.21 mmol) of the above ester in CH$_2$Cl$_2$ (2 mL) was added 0.21 mL (0.84 mmol) of 4.0 M solution of HCl in 1,4-dioxane. The mixture was stirred at room temperature for 3 days during which time a solid precipitated from solution. The solid was collected by filtration, washed with CH$_2$Cl$_2$ and dried under vacuum. The solid was suspended in MeCN (2 mL) and an aqueous solution of potassium carbonate was added. The mixture was washed with CH$_2$Cl$_2$ and the combined organic phase was dried over anhydrous Na$_2$SO$_4$ and absorbed onto silica gel. The residue was purified by flash column chromatography to provide 0.048 g (67%) of the title compound as a yellow solid. MS calc. for C$_{16}$H$_{23}$N$_4$O$_2$S [M+H]$^+$: 335.44. Found: 335.13.

Example 5

Synthesis of 3-amino-6-(4-amino-piperidin-1-yl)-4-(2-morpholin-4-yl-ethoxy)-benzo[b]thiophene-2-carboxylic acid amide

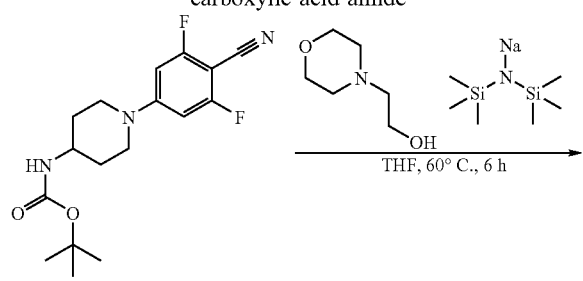

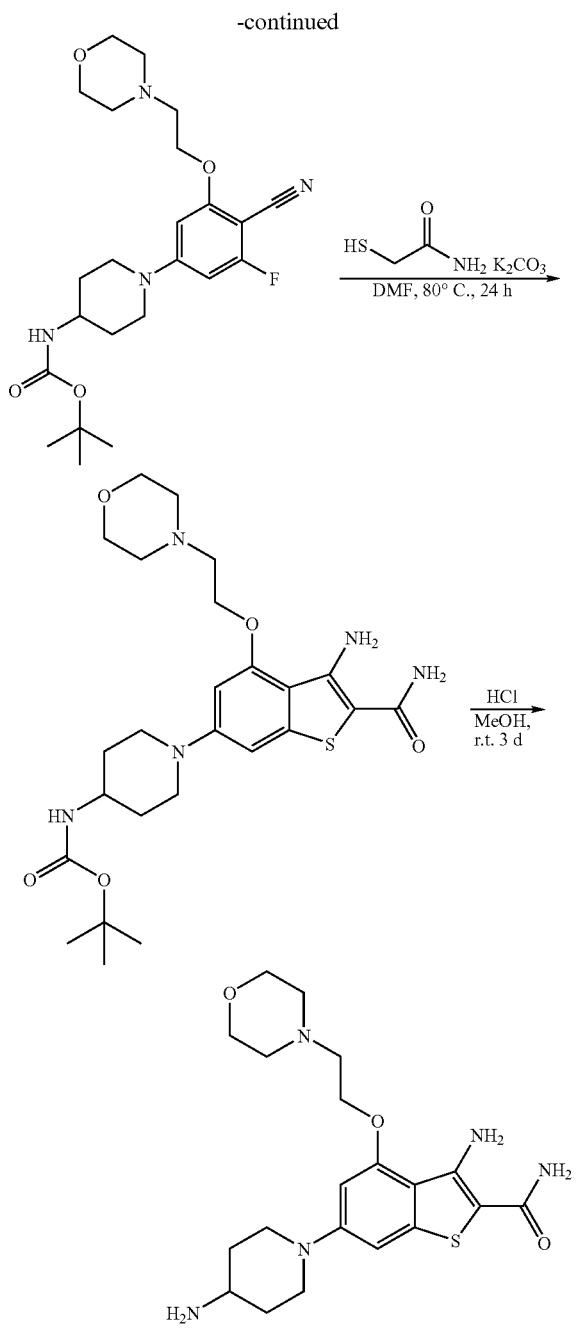

5

To a solution of 0.10 g (0.30 mmol) of [1-(4-cyano-3,5-difluoro-phenyl)-piperidin-4-yl]-carbamic acid tert-butyl ester and 0.040 mL (0.33 mmol) of 4-(2-hydroxyethyl)-morpholine in THF (15 mL), cooled to 0° C., was added 0.60 mL (0.60 mmol) of sodium bis(trimethylsilyl)amide as a 1.0 M solution in THF. The reaction was stirred at 0° C. for 30 min then warmed to 60° C. for 6 h. The reaction was cooled to room temperature and excess base was consumed by the addition of a saturated aqueous solution of NH$_4$Cl. The mixture was diluted with H$_2$O and washed with EtOAc. The combined organic phase was washed with brine, dried over anhydrous Na$_2$SO$_4$ and concentrated under reduced pressure. The crude residue was purified by flash silica gel chromatography to provide 0.081 g (61%) of {1-[4-cyano- 3-fluoro-5-(2-morpholin-4-yl-ethoxy)-phenyl]-piperidin-4-yl}-carbamic acid tert-butyl ester as a white foam.

To a solution of 0.081 g (0.18 mmol) of the above ester in DMF (1 mL) was added 0.45 mL (0.49 mmol) of a 10% solution of 2-thioacetamide in MeOH along with 0.25 g (1.8 mmol) of potassium carbonate. The mixture was heated to 80° C. for 24 h then cooled to room temperature and diluted with H$_2$O. The mixture was washed with CH$_2$Cl$_2$ and the combined organic phase was washed with H$_2$O, dried over anhydrous Na$_2$SO$_4$ and absorbed onto silica gel. The residue was purified by flash silica gel chromatography to provide a 0.069 g (73%) of [1-(3-amino-2-carbamoyl-4-(2-morpholin-4-yl-ethoxy)-benzo[b]thiophen-6-yl)-piperidin-4-yl]-carbamic acid tert-butyl ester as a yellow solid.

To a solution of 0.069 g (0.12 mmol) of the above ester in CH$_2$Cl$_2$ (1 mL) was added 0.50 mL (1.0 mmol) of HCl as a solution in 1,4-dioxane. The mixture was allowed to stir at room temperature for 15 h during which time a solid precipitated from solution. The solid was collected by filtration, washed with CH$_2$Cl$_2$ and dried under vacuum. The solid was dissolved in a 2:1 mixture of MeCN:H$_2$O and potassium carbonate was added to generate the free base. The mixture was diluted with H$_2$O, washed with CH$_2$Cl$_2$ and the combined organic phase was dried over anhydrous Na$_2$SO$_4$ and concentrated under reduced pressure to provide 0.030 g (63%) of the title compound as a yellow solid. MS calc. for C$_{20}$H$_{30}$N$_5$O$_3$S [M+H]$^+$: 420.55. Found: 420.33.

The following compounds were prepared by the procedure described in Example 5, using the appropriate nucleophile in place of 4-(2-hydroxyethyl)-morpholine:

3-Amino-6-(4-amino-piperidin-1-yl)-4-(2-dimethylamino-ethoxy)-benzo[b]thiophene-2-carboxylic acid amide

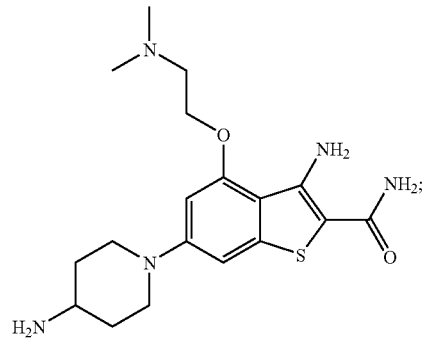

3-Amino-6-(4-amino-piperidin-1-yl)-4-(2,2,2-trifluoro-ethoxy)-benzo[b]thiophene-2-carboxylic acid amide

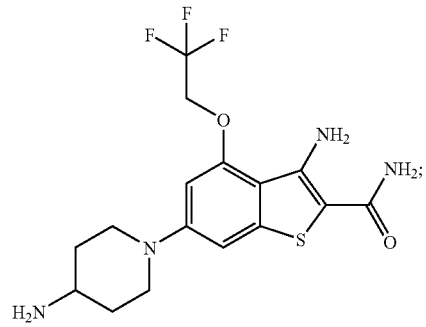

3-Amino-6-(4-amino-piperidin-1-yl)-4-(2-benzylamino-ethoxy)-benzo[b]thiophene-2-carboxylic acid amide

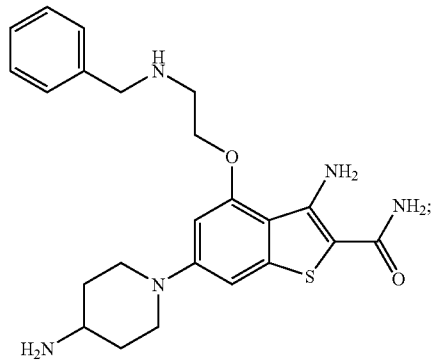

3-Amino-6-(4-amino-piperidin-1-yl)-4-benzyloxy-benzo[b]thiophene-2-carboxylic acid amide

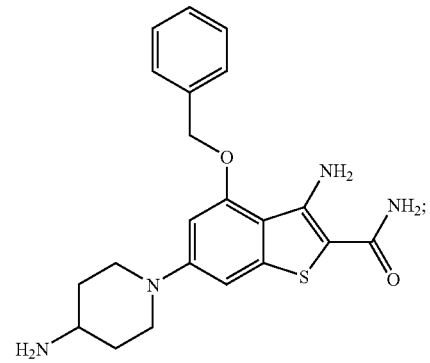

3-Amino-6-(4-amino-piperidin-1-yl)-4-(pyridin-2-ylmethoxy)-benzo[b]thiophene-2-carboxylic acid amide

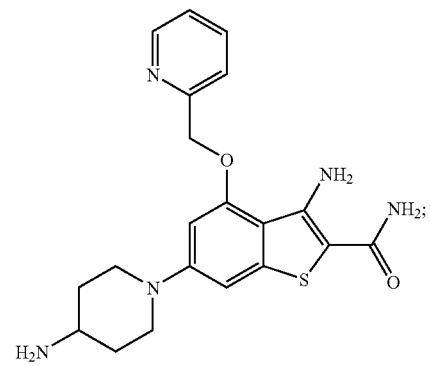

43

3-Amino-6-(4-amino-piperidin-1-yl)-4-(pyridin-3-ylmethoxy)-benzo[b]thiophene-2-carboxylic acid amide

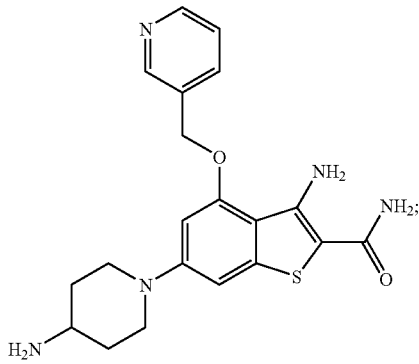

3-Amino-6-(4-amino-piperidin-1-yl)-4-(pyridin-4-ylmethoxy)-benzo[b]thiophene-2-carboxylic acid amide

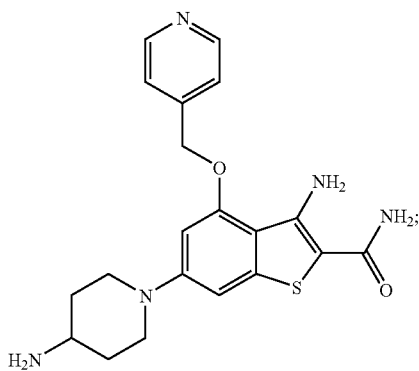

3-Amino-6-(4-amino-piperidin-1-yl)-4-[2-(5-dimethylamino-naphthalene-1-sulfonylamino)-ethoxy]-benzo[b]thiophene-2-carboxylic acid amide

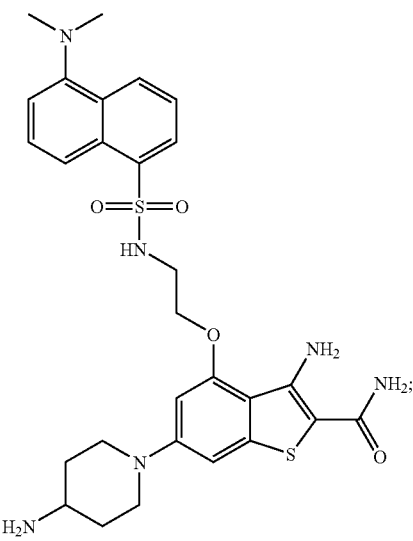

44

3-Amino-6-(4-amino-piperidin-1-yl)-4-(2-benzenesulfonylamino-ethoxy)-benzo[b]thiophene-2-carboxylic acid amide

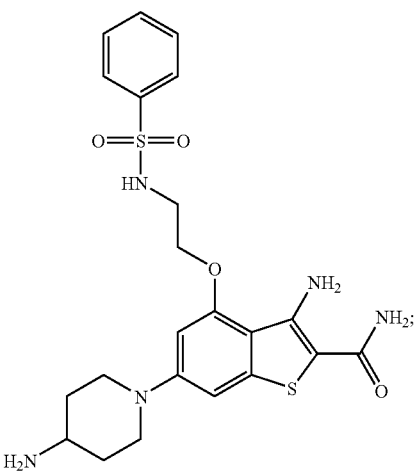

3-Amino-4-(2-amino-ethoxy)-6-(4-amino-piperidin-1-yl)-benzo[b]thiophene-2-carboxylic acid amide

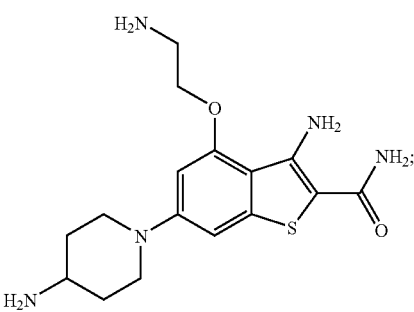

4-(2-Acetylamino-ethoxy)-3-amino-6-(4-amino-piperidin-1-yl)-benzo[b]thiophene-2-carboxylic acid amide

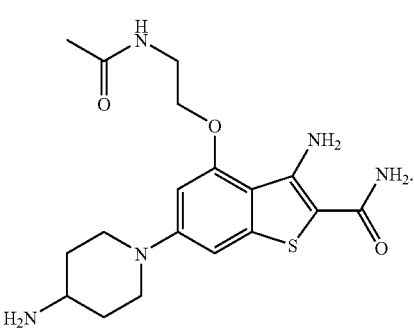

Example 6

Synthesis of 3-Amino-6-(4-amino-piperidin-1-yl)-4-methylsulfanyl-benzo[b]thiophene-2-carboxylic acid amide

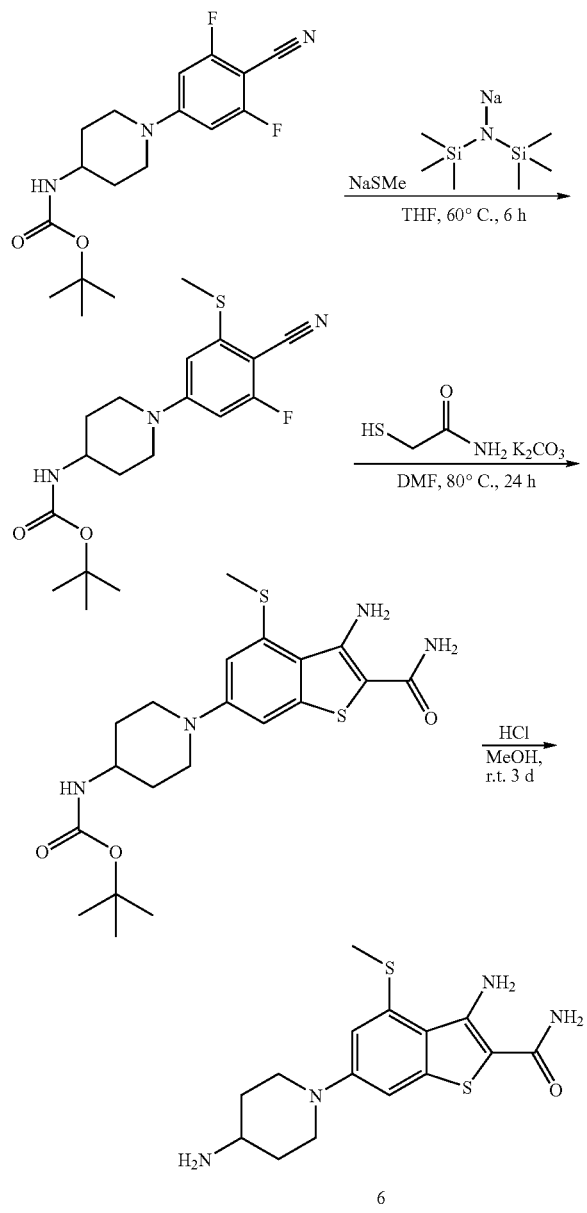

To a solution of 0.50 g (1.48 mmol) of [1-(4-cyano-3,5-difluoro-phenyl)-piperidin-4-yl]-carbamic acid tert-butyl ester in THF (25 mL), cooled to 0° C., was added 0.11 g (1.6 mmol) of sodium thiomethoxide as a solid in one portion. To the mixture was added 1.5 mL (1.5 mmol) of a 1.0 M solution of sodium bis(trimethylsilyl)amide. The reaction was stirred at 0° C. for 30 min then heated to 70° C. for 15 h. The mixture was cooled to room temperature and excess base was consumed by the addition of a saturated aqueous solution of $NH_4Cl$. The mixture was diluted with $H_2O$ and washed with EtOAc. The combined organic phase was washed with brine, dried over anhydrous $Na_2SO_4$, and concentrated under reduced pressure. The residue was purified by flash silica gel chromatography to provide 0.216 g (40%) of 3-amino-6-(4-amino-piperidin-1-yl)-4-methylthio-benzo[b]thiophene-2-carboxylic acid amide as a white solid.

To a solution of 0.211 g (0.577 mmol) of the above amide in DMF (5 mL) was added 1.6 mL (1.8 mmol) of a 10% solution of 2-thioacetamide in MeOH along with 0.80 g (5.8 mmol) of potassium carbonate. The mixture was heated to 70° C. for 15 h then cooled to room temperature and diluted with $H_2O$ which caused a solid to precipitate from solution. The solid was collected by filtration, washed with $H_2O$ and dried under vacuum to provide 0.260 g (100%) of [1-(3-amino-2-carbamoyl-4-methylthio-benzo[b]thiophen-6-yl)-piperidin-4-yl]-carbamic acid tert-butyl ester as a yellow solid.

To a solution of 0.260 g of the above ester in $CH_2Cl_2$ (5 mL) was added 0.60 mL (2.4 mmol) of a 4.0 M solution of HCl in 1,4-dioxane. The mixture was stirred at room temperature for 15 h during which time a solid precipitated from solution. The solid was collected by filtration and then was dissolved in MeOH and the mixture was absorbed onto silica gel. The residue was purified by flash column chromatography to provide a yellow solid which contained a small impurity (approx 10%). The material was further purified by reverse phase preparatory HPLC to provide 0.023 g (12%) of the title compound as a yellow solid. MS calc. for $C_{15}H_{21}N_4OS_2$ [M+H]$^+$: 337.48. Found: 337.34.

Example 7

Synthesis of 3-amino-4-ethoxy-6-(4-hydroxy-piperidin-1-yl)-benzo[b]thiophene-2-carboxylic acid amide

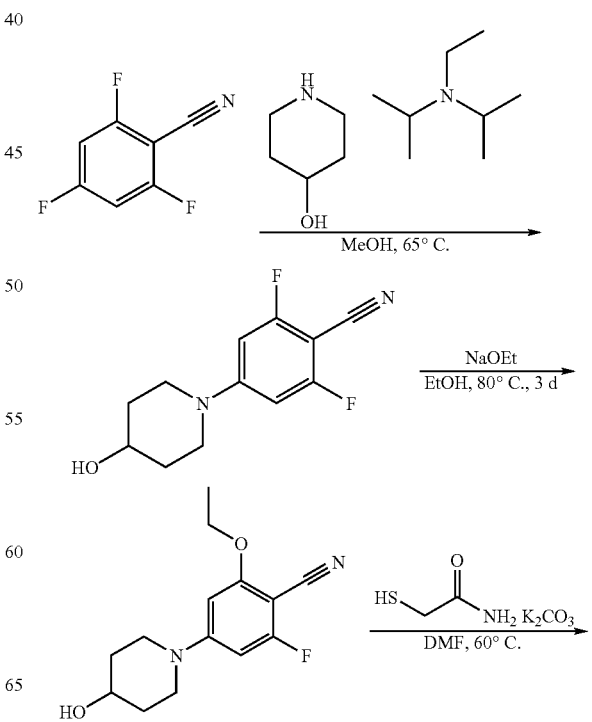

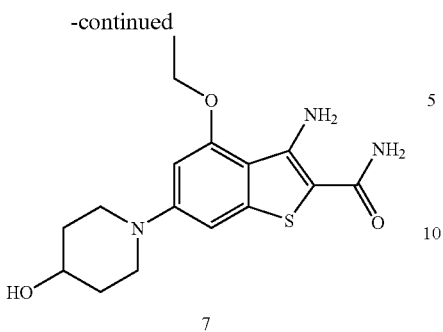

7

To a solution of 1.0 g (6.4 mmol) of 2,4,6-trifluorobenzonitrile in MeOH (35 mL) was added 0.65 g (6.4 mmol) of 4-hydroxypiperidine and 1.2 mL (6.7 mmol) of N,N-diisopropylethylamine. The mixture was heated to 65° C. for 4 h then cooled to room temperature and concentrated under reduced pressure. The residue was purified by flash silica gel chromatography to provide 0.325 g (21%) of 2,6-difluoro-4-(4-hydroxy-piperidin-1-yl)-benzonitrile as a white solid.

To a solution of 0.200 g (0.839 mmol) of the above benzonitrile in EtOH (2 mL), cooled to 0° C., was added 1.0 mL (3.1 mmol) of sodium ethoxide. The reaction was heated to 70° C. for 15 h then cooled to room temperature and an additional 1.0 mL (3.1 mmol) of sodium ethoxide was added. The mixture was heated to 70° C. for an additional 15 h. The reaction was cooled to room temperature and excess base was consumed by the addition of a saturated aqueous solution of $NH_4Cl$. The mixture was diluted with $H_2O$ and washed with $CH_2Cl_2$. The combined organic phase was dried over anhydrous $Na_2SO_4$ and concentrated under reduced pressure. The residue was purified by flash silica gel chromatography to provide after 0.048 g (21%) of 2-ethoxy-6-fluoro-4-(4-hydroxy-piperidin-1-yl)-benzonitrile as a white solid.

To a solution of 0.047 g 0.18 mmol) of 2-ethoxy-6-fluoro-4-(4-hydroxy-piperidin-1-yl)-benzonitrile in DMF (2 mL) was added 0.50 mL (0.55 mmol) of a 10% solution of 2-thioacetamide in MeOH along with 0.250 g (1.8 mmol) of potassium carbonate. The mixture was heated to 50° C. for 3 days then cooled to room temperature and diluted with $H_2O$. The mixture was washed with $CH_2Cl_2$ and the combined organic phase was washed with $H_2O$, dried over anhydrous $Na_2SO_4$ and concentrated under reduced pressure. The residue was purified by flash silica gel chromatography to provide 0.046 g (77%) of the title compound as a yellow powder. MS calc. for $C_{16}H_{22}N_3O_3S$ $[M+H]^+$: 336.43. Found: 336.32.

Example 8

Synthesis of 3-amino-4-ethoxy-7-methanesulfonylamino-benzo[b]thiophene-2-carboxylic acid amide

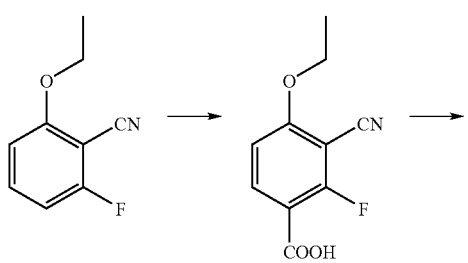

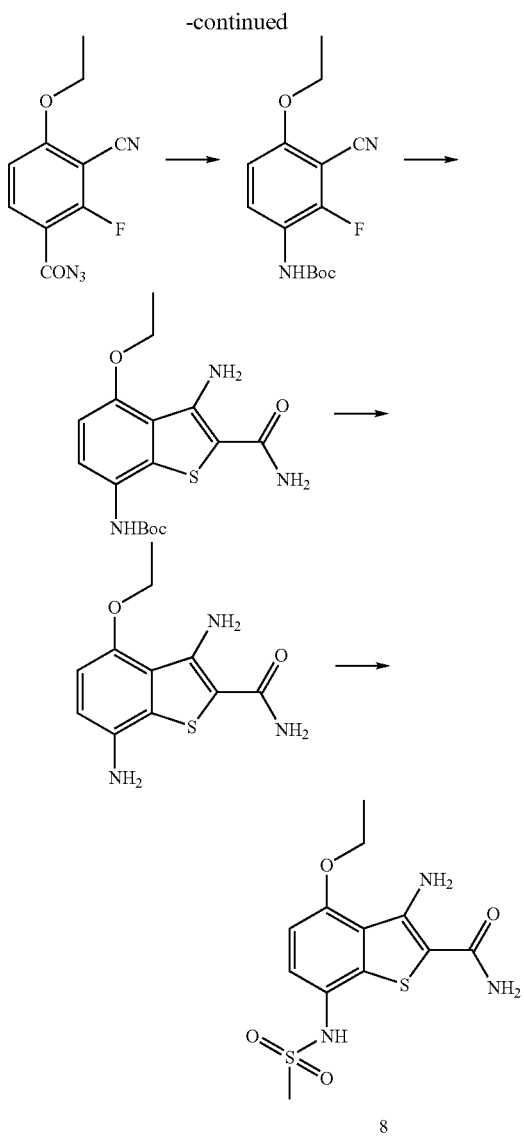

8

To a stirred solution of 2-ethoxy-6-fluorobenzonitrile (J. Hynes, *J. Heterocycl. Chem.* 1988, 25, 1173) (10.0 g, 60.54 mmol) in THF (150 mL) at −78° C. was added lithium diisopropylamide (1.8 M, 44.1 mL, 79.4 mmol). The mixture was stirred at −78° C. for 1 h. Then it was poured slowly onto dry ice and stirred until it reached room temperature. The mixture was concentrated to about 10 mL, then diluted with 6N HCl (200 mL), and extracted with dichloromethane (3×100 mL). The solvent was washed with brine and dried over $Na_2SO_4$. The solvent was removed to give product 3-cyano-4-ethoxy-2-fluorobenzoic acid (4.2 g, 33.2%).

To a stirred solution of the above benzoic acid intermediate (3 g, 14.34 mmol) and triethylamine (4.5 g, 44.47 mmol) in dry THF (30 mL) at −10° C. was added ethyl chloroformate (2.5 g, 23.04 mmol). The reaction was stirred for 1 h and monitored by TLC (20% EtOAc in $CH_2Cl_2$). A solution of $NaN_3$ (2.3 g, 35.34 mmol) in water (15 mL) was added dropwise to the mixture and stirred for 2 h. The mixture was diluted with water (40 mL) and extracted with toluene (3×20 mL). The extract was washed with brine and dried over Na$_2$SO$_4$. The solvent was removed in vacuo to give 3-cyano-4-ethoxy-2-fluoro-benzoyl azide (2.5 g, 39.2%).

A mixuture of the above azide intermediate (2.5 g, 12.13 mmol), t-BuOH (20 mL) and toluene (15 mL) was stirred at 110° C. overnight. The solvent was removed in vacuo. Flash chromatography (20-50% EtOAc in hexane) afforded 3-N-Boc-amino-6-ethoxy-2-fluorobenzonitrile (2.05 g, 60.3%).

To a stirred solution of the above benzonitrile intermediate (1.0 g, 3.57 mmol) in dry DMSO (15 mL) was added 2-mercaptoacetamide (5.6 mL, 5.5 mmol) and sodium ethoxide (1.5 mL, 4.0 mmol). The reaction was stirred at 80° C. for 4 h. The reaction was then diluted with water and the resulting precipitates were filtered and washed with MeOH (10 mL) to give 3-amino-4-ethoxy-7-N-Boc-amino-benzo[b]thiophene-2-carboxylic acid amide (0.95 g, 75.8%).

To a stirred solution of the above amide (0.95 g, 2.7 mmol) in dry dioxane (10 mL) was added 4 M HCl (in dioxane, 15 mL). The reaction was stirred at room temperature for 3 h. It was then concentrated and dried in vacuo to give 3,7-diamino-4-ethoxy-benzo[b]thiophene-2-carboxylic acid amide as yellow solid (0.8 g, 100%).

To a stirred mixture of the above amide (0.2 g, 0.8 mmol) and pyridine (2.0 mL) in THF at 0° C. was added methanesulfonyl chloride (0.46 g, 4.0 mmol). The reaction was stirred at room temperature overnight. It was next diluted with water and extracted with dichloromethane (20 mL). The solvent was removed and purified by preparative TLC (5% EtOAc in CH$_2$Cl$_2$) to afford the title compound (20 mg, 7.6%).

Example 9

Synthesis of 3-amino-6-bromo-4-cyclopentyl-methoxy-benzo[b]thiophene-2,7-dicarboxylic acid diamide

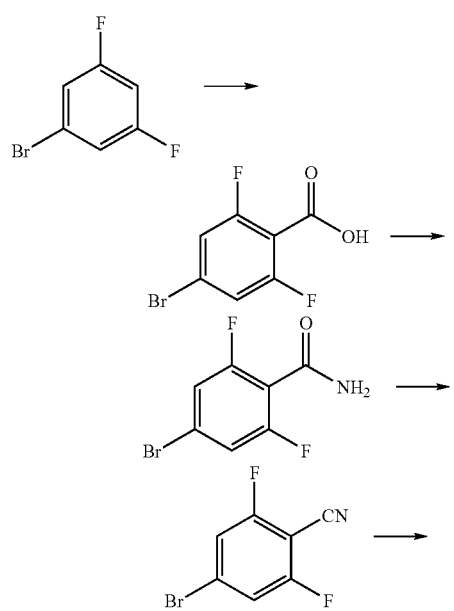

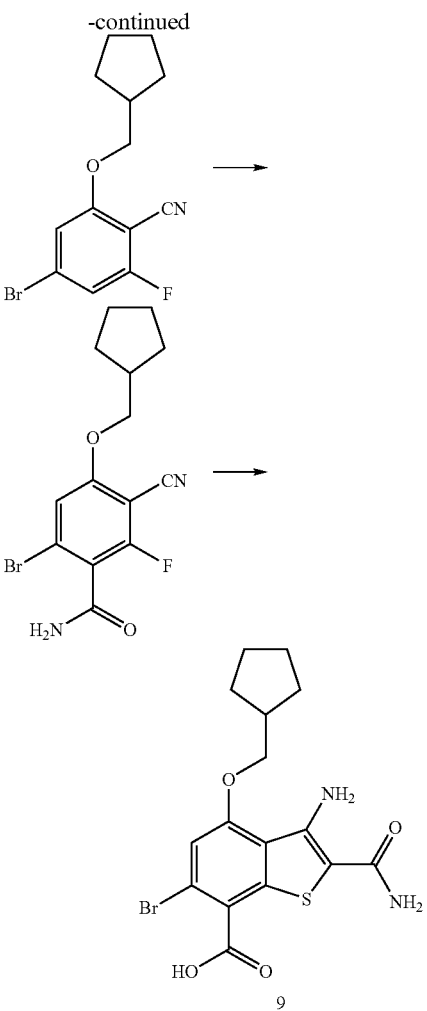

To a stirred solution of 3,5-difluorobromobenzene (20 g, 103.6 mmol) in THF (200 mL) at −78° C. was added lithium diisopropylamide (2.0 M, 51 mL, 103 mmol). The reaction was stirred for 1.5 h. Then it was poured slowly onto dry ice and stirred until it reached room temperature. The mixture was concentrated to about 10 mL and then diluted with 6 N HCl (200 mL), extracted with dichloromethane (200 mL). The solution was dried over Na$_2$SO$_4$ and the solvent was removed in vacuo to give 4-bromo-2,6-difluorobenzoic acid (18 g, 73.3%).

To a stirred solution of the above benzoic acid intermediate (18 g, 76 mmol) in THF (150 mL)), at −20° C., was added triethylamine (7.6 g, 76 mmol) and ethyl chloroformate (9.8 g, 91 mmol. The reaction was stirred at −20° C. for 20 min. Then it was warmed up to room temperature and an ammonia solution (0.5 M in dioxane, 150 mL, 76 mmol) was added. The reaction was stirred at room temperature overnight. It was then concentrated, diluted with dichloromethane, washed with 1 N HCl and brine, and dried over Na$_2$SO$_4$. The solvent was removed to give the crude product as a solid. It was washed with dichloromethane to give 4-bromo-2,6-difluorobenzamide (9.4 g, 52.4%).

To a stirred solution of the above benzamide intermediate (9.4 g, 40 mmol) in DMF (15 mL) was added cyanuric chloride (7.24 g, 40 mL) at 0° C. The reaction was stirred at 0° C. for 3 h. Water was added slowly to the reaction and it was extracted with CH$_2$Cl$_2$ (3×100 mL). The solvent was washed with brine and dried over Na$_2$SO$_4$. The solvent was removed to give 4-bromo-2,6-difluorobenzonitrile (7.57 g, 86.9%).

To a stirred solution of the above benzonitrile intermediate (7.5 g, 34.4 mmol) in dry THF (50 mL) at 0° C. was added a mixture of sodium bis(trimethylsilyl)amide (1.0 M, 34 mL, 34 mmol) and cyclopentanemethanol (3.4 g, 34 mmol) in THF (100 mL). The reaction was allowed to warm up to room temperature and stirred overnight. Water (50 mL) was added to the reaction and the product was extracted by CH$_2$Cl$_2$ (2×50 mL). The solvent was washed with brine and dried over Na$_2$SO$_4$. The solvent was removed to give 4-bromo-2-cyclopentylmethoxy-6-fluorobenzonitrile (4.5 g, 43.9%).

To a stirred solution of the above benzonitrile intermediate (4.5 g, 15.1 mmol) in THF (100 mL) was added lithium diisopropylamide (2.0 M in THF, 8 mL, 16 mmol) at −78° C. The mixture was stirred at −78° C. for 1 h, then it was poured slowly onto dry ice and stirred until it reached room temperature. The mixture was concentrated to 10 mL, diluted with 6 N HCl (150 mL) and extracted with CH$_2$Cl$_2$ (3×100 mL). The solution was washed with brine and dried with Na$_2$SO$_4$. The solvent was removed to give 3-cyano-6-bromo-4-cyclopentylmethoxy-2-fluorobenzoic acid (2.1 g, 40.7%).

To a stirred solution of the above benzoic acid intermediate (0.2 g, 0.59 mmol) in dry THF (15 mL) was added ammonia (0.5 M in dioxane, 1.2 mL, 0.6 mmol), N,N-diisopropylethylamine (0.23 g, 1.8 mmol) and PyBOP (0.312 g, 0.6 mmol). The mixture was stirred overnight at room temperature. 2-Mercaptoacetamide (0.8 mL, 0.9 mmol) was added and the reaction was heated at 80° C. for 2 h. Sodium ethoxide (0.5 mL, 1.2 mmol) was added and the reaction was stirred for 4 h at 80° C. Then it was diluted with 2N NaOH at room temperature. The precipitates were filtered to give the product title compound (0.11 g, 45.6%).

Example 10

Synthesis of 3-amino-4-methoxy-benzo[b]thiophene-2,7-dicarboxylic acid 2-amide 7-methylamide; compound with methoxy-benzene

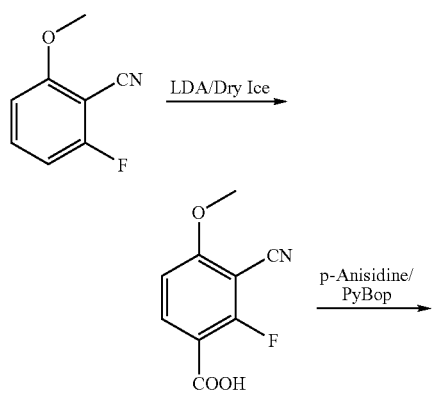

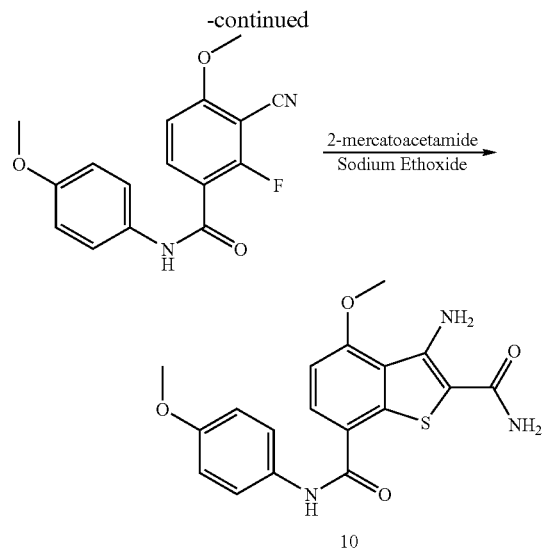

To a stirred lithium diisopropylamide solution (1.8M in heptane/THF/ethylbenzene, 44.1 mL, 79.4 mmol) at −50° C. was added a solution of 2-fluoro-6-methoxybenzonitrile (10 g, 66.16 mmol) in THF (80 mL) slowly and stirring was continued at that temperature for 1 h. The reaction mixture was poured onto a stirred slurry of dry ice in dry THF (100 mL). After the mixture had warmed up to room temperature, it was concentrated to about 50 mL, diluted with 6 N HCl (200 mL), extracted with dichloromethane, dried with sodium sulfate, concentrated, and dried in vacuo to give 3-cyano2-fluoro-4-methoxybenzoic acid (12.9 g, 100%).

A mixture of the above benzoic acid derivative (360 mg, 1.85 mmol), p-anisidine (315 mg, 2.56 mmol), N,N-diisopropylethylamine (1.34 mL, 7.68 mmol) and PyBop (1.6 g, 3.1 mmol) in dry DMF (7 mL) was stirred at room temperature overnight and then diluted with water (40 mL). The precipitates were filtered, washed with water three times, and dried in vacuo to give 3-cyano-2-fluoro-4-methoxy-N-(4-methoxy-phenyl)-benzamide (540 mg, 98%).

To a stirred solution of the above benzamide intermediate (222 mg, 0.74 mmol) in dry DMSO (2 mL) was added a solution of 2-mercaptoacetamide in MeOH (1.11 M, 1 mL, 1.11 mmol) and sodium ethoxide (2.68 M in EtOH, 0.83 mL, 2.22 mmol). The reaction was heated at 70° C. overnight and, after it had cooled to room temperature, diluted with water (10 mL). The precipitate was filtered, washed with water three times, and dried in vacuo to give the title compound (208 mg, 0.56 mmol, 75.7%).

Example 11

Synthesis of 3-amino-6-(2-amino-ethyl)-4-cyclopentylmethoxy-benzo[b]thiophene-2-carboxylic acid amide

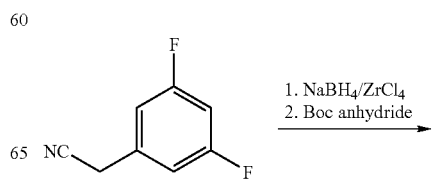

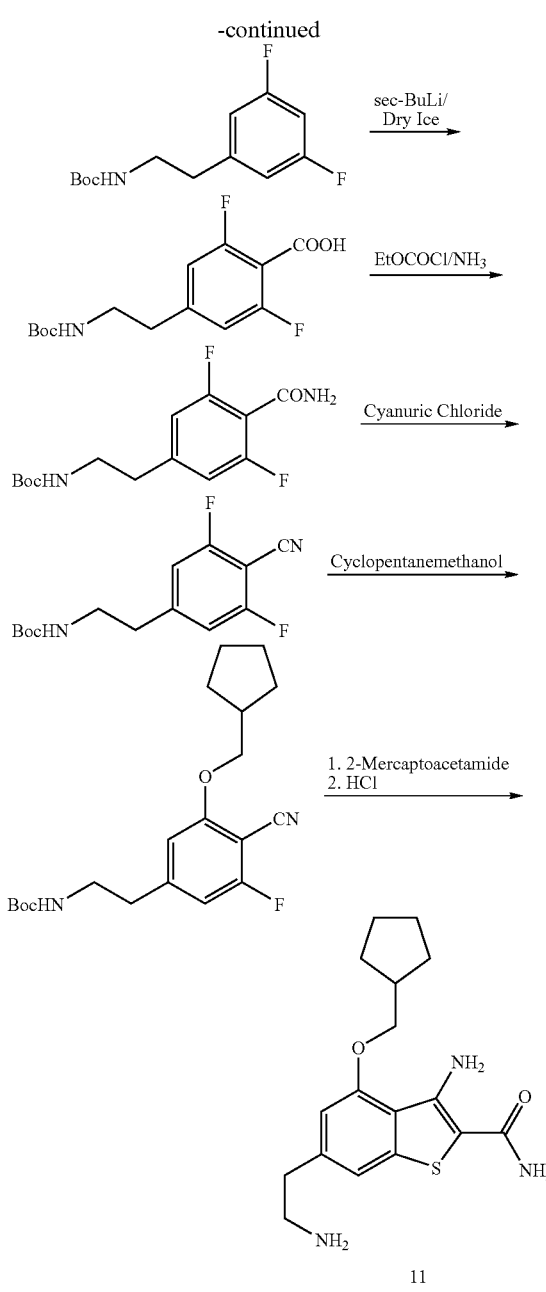

11

To a stirred mixture of ZrCl$_4$ (30 g) in THF (400 mL) was slowly added NaBH$_4$ (26 g) at 0° C., and then a solution of 3,5-difluorophenylacetonitrile (11 g, 71.8 mmol) in THF (100 mL). The reaction was allowed to warm to room temperature and was stirred overnight. It was carefully quenched with water at 0° C. and then stirred with dichloromethane (300 mL) for 10 min. It was filtered and the filtrate was extracted with dichloromethane, washed with brine, dried with sodium sulfate, concentrated, and dried in vacuo to give the crude phenylethylamine intermediate (11.5 g).

The crude amine intermediate and Boc anhydride (18.44 g, 84.5 mmol) were stirred with triethylamine (11.85 mL, 85.0 mmol) in acetonitrile (100 mL) at room temperature for 2 days. It was then concentrated, diluted with water, extracted with dichloromethane, washed with brine, dried with sodium sulfate, concentrated, and purified by chromatography on silica gel (hexane/dichloromethane, 1:1) affording N-boc-2-(3,5-difluorophenylethylamine (6.7 g, 36.3%).

To a stirred solution of the above amine (1.05 g, 4.08 mmol) and tetramethylethylenediamine (0.62 mL, 4.08 mmol) in THF (50 mL) at −78° C. was added sec-BuLi (1.3 M in cyclohexane, 12.6 mL, 16.38 mmol) and the solution was stirred at that temperature for 2 h before it was poured to a mixture of dry ice in ether. It was next diluted with 6N HCl, extracted with dichloromethane, dried with sodium sulfate, concentrated, and dried in vacuo to give 4-(N-boc-2-aminoethyl)-2,6-difluorobenzoic acid (1.23 g, 100%).

To a stirred solution of the above benzoic cid intermediate (1.23 g, 4.08 mmol) and triethylamine (0.63 mL, 4.5 mmol) in THF (20 mL) at −25° C. was added ethyl chloroformate (0.43 mL, 4.5 mmol). The reaction was warmed to 0° C. in 1 h and an ammonia solution (0.5 N in dioxane, 20 mL, 10 mmol) was then added. The reaction was stirred at room temperature overnight, concentrated, diluted with dichloromethane, washed with 1N HCl and brine, dried with sodium sulfate, concentrated, and dried in vacuo to give 4-(N-boc-2-aminoethyl)-2,6-difluorobenzamide (0.8 g, 65%).

To a stirred solution of the above benzamide intermediate (1.5 g, 5.0 mmol) in DMF (15 mL) at 0° C. was added cyanuric chloride (0.461 g, 2.5 mmol). The reaction was stirred at 0° C. for 40 min. Water (50 mL) was added and the mixture was extracted with dichloromethane, dried with sodium sulfate and concentrated. Chromatography on silica gel (ether/hexane, 1:1) afforded 4-(N-boc-2-aminoethyl)-2,6-difluorobenzonitrile (1.1 g, 3.9 mmol, 78%).

To a stirred solution of the above benzonitrile intermediate (8.66 mmol) and cyclopentanemethanol (781 mg, 7.8 mmol) in THF (45 mL) at 0° C. was added N-sodium hexamethyldisilazane (1 M in THF, 7.8 mL, 7.8 mmol) and the reaction was stirred overnight. It was diluted with water, extracted with dichloromethane, washed with brine, dried with sodium sulfate, concentrated and dried in vacuo to give 4-(N-boc-2-aminoethyl)-2-cyclopentylmethoxy-6-fluorobenzonitrile (1.27 g, 3.5 mmol, 45%).

A stirred mixture of the above benzonitrile intermediate (0.6 g, 1.655 mmol), 2-mercaptoacetamide (1.11 M in MeOH, 2.7 mL, 3.0 mmol), and NaOEt (2.68 M in EtOH, 1.12 mL, 3.0 mmol) in DMF (4 mL) was heated at 70° C. overnight. The reaction was then cooled to room temperature and diluted with water. The precipitates were filtered to give the Boc protected intermediate (0.642 g, 89%). This intermediate (0.4 g, 0.923 mmol) was dissolved in THF (5 mL), and HCl (4 N in dioxane, 5 mL, 20 mmol) was added. The reaction was allowed to sit for 2 h. Ether was then added and the precipitates were filtered to give the title compound as the HCl salt (0.29 g, 0.78 mmol, 85%).

Example 12

Synthesis of 3-amino-7-cyano-4-cyclobutoxy-benzo[b]thiophene-2-carboxylic acid amide

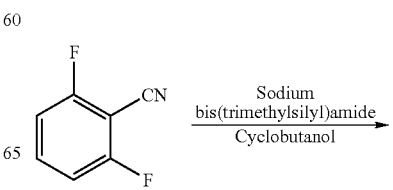

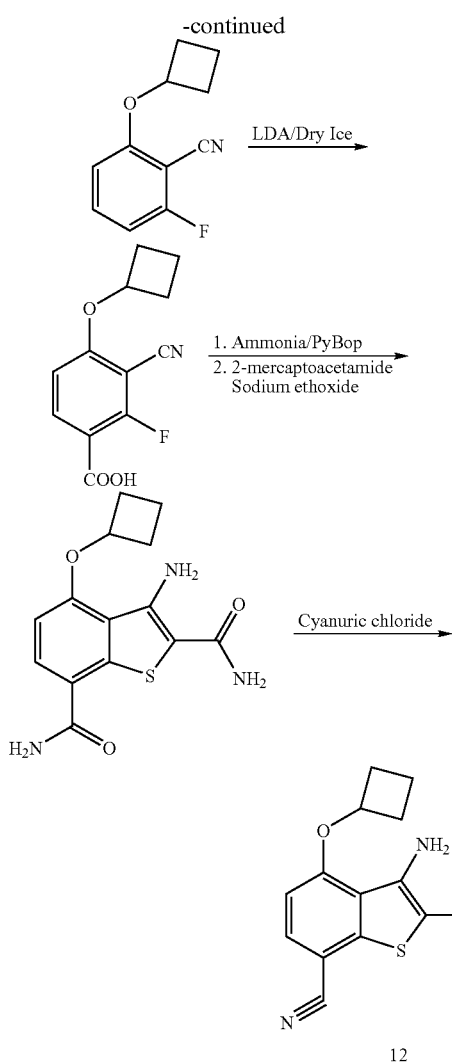

A mixture of sodium bis(trimethylsilyl)amide (1 M in THF, 21.6 mL, 21.6 mmol) and cyclobutanol (1.56 g, 21.6 mmol) was stirred for 20 min at room temperature. It was then added to a stirred solution of 2,6-difluorobenzonitrile (3.00 g, 21.57 mmol) in THF (30 mL) at 0° C. The reaction was allowed to warm to room temperature and was stirred overnight. It was then diluted with water (150 mL) and extracted with dichloromethane.

The organic phase was rinsed with brine, dried over sodium sulfate, concentrated, and dried in vacuo to give 2-cyclobutyloxy-6-fluorobenzonitrile (3.70 g, 19.35 mmol, 89.7%).

A solution of the above benzonitrile intermediate (3.00 g, 15.69 mmol) in THF (150 mL) was cooled to −78° C. Lithium diisopropylamide solution (1.8M in heptane/THF/ethylbenzene, 10.0 mL, 18.0 mmol) was added and the mixture was stirred for 1 h. It was then poured slowly onto dry ice and allowed to warm to room temperature. The mixture was concentrated to about 10 mL and diluted with 6 N HCl (200 mL). It was then extracted with dichloromethane, rinsed with brine, dried over sodium sulfate, and concentrated. The crude product was washed with dichloromethane and dried in vacuo to give 3-cyano-4-cyclobutyloxy-2-fluorobenzoic acid (3.10 g, 13.18 mmol, 84.0%).

To a stirred solution of the above benzoic acid intermediate (2.00 g, 8.50 mmol) in THF (20 mL) was added an ammonia solution (0.5M in 1,4-dioxane, 17.0 mL, 8.50 mmol), diisopropylethylamine (3.36 g, 26.0 mmol) and PyBOP (4.43 g, 8.50 mmol). The solution was stirred at room temperature overnight then 2-mercaptoacetamide (1.1 M in MeOH, 11.6 mL, 12.76 mmol) was added and the reaction was heated at 80° C. for 3 h. Sodium ethoxide (2.68 M in EtOH, 4.80 mL, 12.86 mmol) was added and the reaction continued for 4 h. After cooling to room temperature, the reaction was diluted with 2 N sodium hydroxide solution (100 mL). The precipitate formed was collected by filtration, washed with MeOH and dried in vacuo to give 3-amino-4-cyclobutoxy-benzo[b]thiophene-2,7-dicarboxylic acid diamide (0.850 g, 2.784 mmol, 32.7%).

To a stirred solution of the above amide (200 mg, 0.655 mmol) in DMF (3 mL) was added cyanuric chloride (60 mg, 0.325 mmol). The reaction was stirred at room temperature for 1 h. The mixture was slowly diluted with water (10 mL) and extracted with dichloromethane. The aqueous phase was allowed to stand for two weeks then the precipitate formed was collected by filtration, rinsed with MeOH and dried in vacuo to give the title compound (93.5 mg, 0.315 mmol, 48.1%).

Example 13

Synthesis of 3-amino-4-ethoxy-7-hydroxymethyl-benzo[b]thiophene-2-carboxylic acid amide

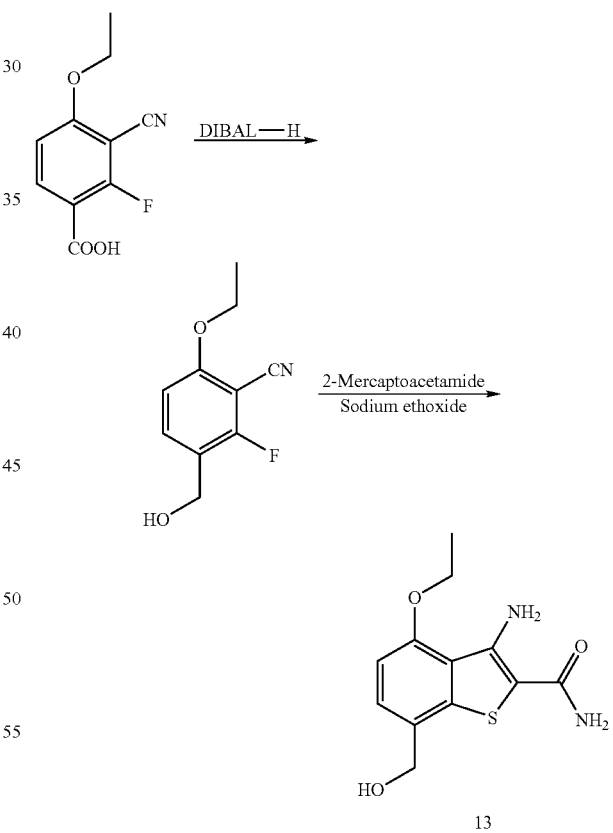

To a stirred solution of 3-cyano-4-ethoxy-2-fluorobenzoic acid (3.0 g, 14.34 mmol) in THF (16 mL) and ether (8 mL) at −78° C. was added diisobutylaluminum hydride (DIBAL-H) solution (1 M in THF, 43.0 mL, 43.0 mmol). The reaction was allowed to warm to 0° C. over 3 h, and then it was stored at −10° C. overnight. 1M Sodium potassium tartrate (100 mL, 100 mmol) and diatomaceous earth were added and stirred at room temperature for 4 h. The mixture was filtered through a diatomaceous earth pad, extracted with dichloromethane, rinsed with saturated sodium bicarbonate solution, and rinsed with brine. It was dried over sodium sulfate, concentrated and dried in vacuo to give 6-ethoxy-3-hydroxymethyl-2-fluorobenzonitrile (2.352 g, 12.05 mmol, 63.0%) which was used as is in the next reaction.

To a stirred solution of the above benzonitrile intermediate (500 mg, 2.56 mmol) in dry DMF (3 mL) was added 2-mercaptoacetamide (1.1 M in MeOH, 3.50 mL, 3.85 mmol) and sodium ethoxide (2.68 M in EtOH, 1.05 mL, 2.81 mmol). The reaction was stirred at 80° C. overnight, and then it was cooled to room temperature and diluted with 2 M sodium hydroxide solution (30 mL). The precipitate formed was collected by filtration, and dried in vacuo to give the title compound (0.455 g, 1.71 mmol, 88.9%).

Example 14

Synthesis of 3-amino-4-ethoxy-benzo[b]thiophene-2,7-dicarboxylic acid diamide

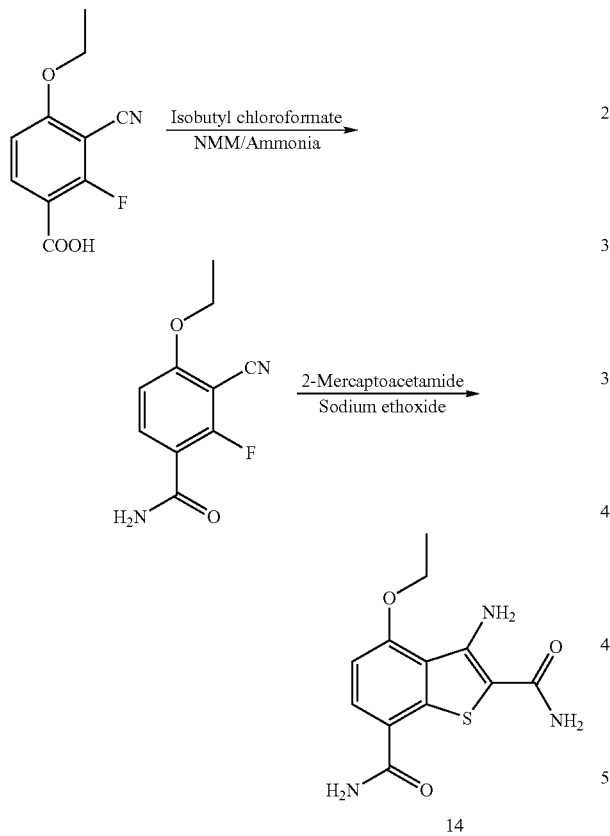

To a stirred solution of 3-cyano-4-ethoxy-2-fluorobenzoic acid (500 mg, 2.39 mmol) and N-methylmorpholine (0.526 mL, 4.78 mmol) in THF (4 mL) at 0° C. was added isobutyl chloroformate (0.310 mL, 2.39 mmol). After 10 min a solution of ammonia (0.5 M in 1,4-dioxane, 5.259 mL, 2.63 mmol) in THF (5 mL) was added. The reaction was allowed to warm to room temperature and stirred overnight. It was concentrated then diluted with MeOH and the insoluble material filtered off. Silica gel chromatography (0-5% MeOH/dichloromethane) gave 3-cyano-4-ethoxy-3-fluorobenzamide (0.120 g, 0.576 mmol, 12.8%).

To a stirred solution of the above benzamide (0.120 g, 0.575 mmol) in DMSO (3 mL) was added 2-mercaptoacetamide (1.1 M in MeOH, 0.787 mL, 0.866 mmol) and sodium ethoxide (2.68 M in EtOH, 0.237 mL, 0.635 mmol).

The reaction was stirred at 70° C. overnight. It was cooled to room temperature then diluted with 2 M sodium hydroxide solution (20 mL). The precipitate formed was collected by filtration, and dried in vacuo to give the title compound (71 mg, 0.254 mmol, 83.9%).

Example 15

Synthesis of 3-amino-7-isopropylamino-4-methoxy-benzo[b]thiophene-2-carboxylic acid amide

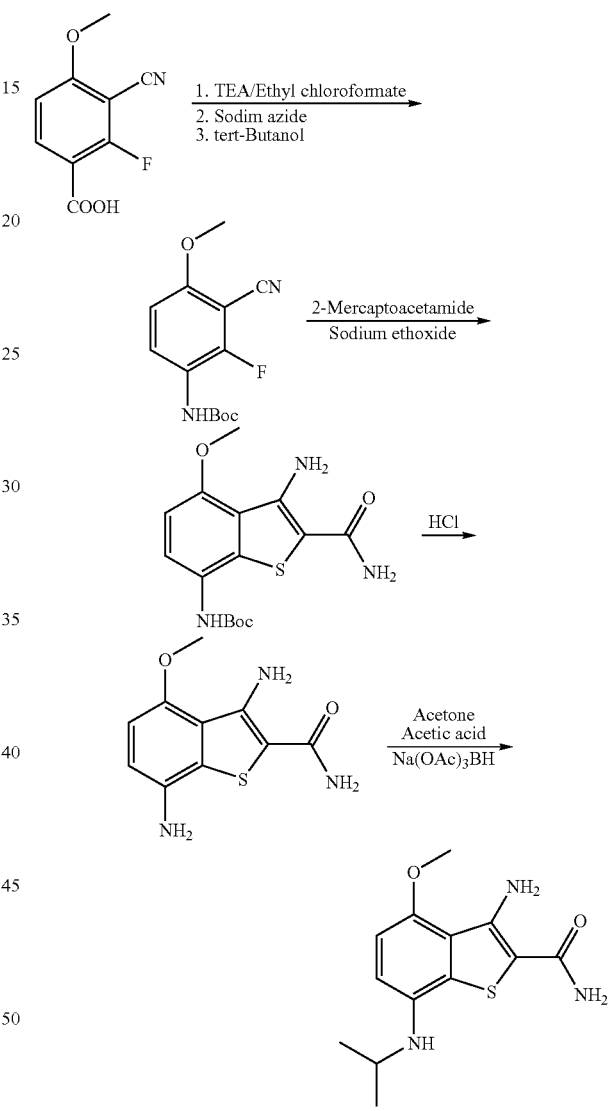

To a stirred solution of 3-cyano-4-ethoxy-2-fluorobenzoic acid (1.00 g, 5.12 mmol) and triethylamine (1.428 mL, 10.248 mmol) in THF (15 mL) at −10° C. was added ethyl chloroformate (1.23 mL, 12.81 mmol). The reaction was stirred in an ice bath for 2 h. A solution of sodium azide (1.33 g, 20.50 mmol) in water (8 mL) was added dropwise and the mixture stirred for 2 h. It was then diluted with water (75 mL) and extracted with toluene (3×20 mL). The combined organic phase was rinsed with brine, dried over sodium sulfate and concentrated to about 30 mL. tert-Butanol (50 mL) was added and the reaction refluxed at 130° C. for 4 h. It was concentrated and purified by silica gel chromatography (0-5% EtOAc in dichloromethane) to give N-Boc-3-amino-2-fluoro-6-methoxybenzonitrile (440 mg, 1.65 mmol, 32.3%).

To a stirred solution of the above benzonitrile intermediate (100 mg, 0.376 mmol) in DMSO (1 mL) was added 2-mercaptoacetamide solution (1.1 M in MeOH, 0.514 mL, 0.565 mmol) and sodium ethoxide (2.68 M in EtOH, 0.155 mL, 0.415 mmol). The reaction was stirred at 70° C. overnight then it was cooled to room temperature and diluted with water (5 mL). The precipitate formed was collected by filtration, and dried in vacuo to give 7-N-Boc-3,7-diamino-4-methoxy-benzo[b]thiophene-2-carboxylic acid amide (111 mg, 0.329 mmol, 87.5%).

To a stirred solution of the above amide (111 mg, 0.329 mmol) in dioxane (2 mL) and dry MeOH (0.5 mL) was added HCl (4 M in dioxane, 10 mL, 40 mmol). The reaction was stirred at room temperature for 2 h. The mixture was concentrated and dried in vacuo to give 3,7-diamino-4-methoxy-benzo[b]thiophene-2-carboxylic acid amide as the HCl salt (110 mg, 100%).

To a stirred solution of the above HCl salt (63 mg, 0.188 mmol) in DMF (5 mL) was added acetone (0.028 mL, 0.376 mmol), sodium triacetoxyborohydride (120 mg, 0.564 mmol) and glacial acetic acid (0.032 mL, 0.564 mmol). The mixture was stirred at room temperature for 4 days, and then it was quenched with sodium bicarbonate solution. It was extracted with dichloromethane, washed with brine and concentrated. Silica gel chromatography (0-33% EtOAc in dichloromethane) gave the title compound (21 mg, 0.075 mmol, 40.0%).

Example 16

Synthesis of 3-amino-7-furan-4-trifluoromethyl-benzo[b]thiophene-2-carboxylic acid amide To a solution of 2 M n-BuLi in pentane (1.62 mL, 3.24 mmol) in 8 mL of dry THF under $N_2$ at −78° C. was added 2-fluoro-6-(trifluoromethyl)benzonitrile (612 mg, 3.24 mmol) in 2 mL of dry THF. The mixture was stirred at −78° C. for 30 min, followed by the addition of iodine (1070 mg, 4.22 mmol) in 2 mL of dry THF. The reaction mixture was warmed up and stirred for 2 h at room temperature. Water was added followed by a solution of $Na_2S_2O_3$. The mixture was extracted with EtOAc. The organic layer was separated and washed with water and brine. The organic layer was dried over anhydrous $MgSO_4$, filtered and concentrated. The residue was purified by silica gel chromatography eluting with 5% EtOAc/hexane. The product fractions were collected and concentrated to afford 180 mg (17.7%) of 2-fluoro-3-iodo-6-trifluoromethylbenzonitrile as a brown dark solid.

To the above benzonitrile intermediate (140 mg, 0.444 mmol) in 4 mL of MeOH was added 2-mercaptoacetamide (100 mg/mL in MeOH-ammonia solution) (0.49 mL, 0.533 mmol) and 0.5M sodium methoxide in MeOH (1.78 mL, 0.89 mmol). The reaction mixture was stirred at room temperature for 18 h. The mixture was concentrated and purified by silica gel chromatography eluting with 2-5% MeOH/$CH_2Cl_2$. The product fractions were collected and concentrated to afford 79 mg (46%) of 3-amino-7-iodo-4-trifluoromethyl-benzo[b]thiophene-2-carboxylic acid amide as a yellow crystalline solid.

To a sealed tube was added the above amide intermediate (20 mg, 0.0518 mmol), furan-3-boronic acid (9.5 mg, 0.085 mmol) and tetrakis(triphenylphosphine)palladium(0) (12 mg, 0.0104 mmol) in 1 mL of dimethoxyethane, followed by the addition of 0.3 mL of 20% $Na_2CO_3$. The mixture was heated at 85° C. for 18 h. The reaction mixture was filtered and concentrated. The residue was purified by silica gel chromatography eluting with 0-5% MeOH/$CH_2Cl_2$. The product fractions were collected and concentrated to afford 9 mg (53.2%) of the title compound as yellow solid product.

The following compounds were prepared from 3-amino-7-iodo-4-trifluoromethyl-benzo[b]thiophene-2-carboxylic acid amide using the coupling procedure described Example 16 with the appropriate aryl or heteroaryl boronic acid intermediate:

3-Amino-7-pyridin-3-yl-4-trifluoromethyl-benzo[b]thiophene-2-carboxylic acid amide

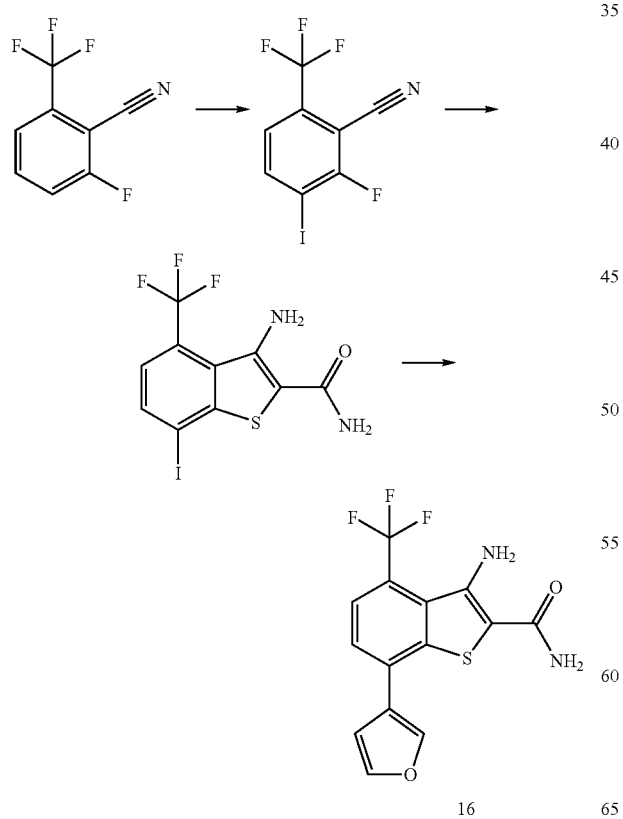

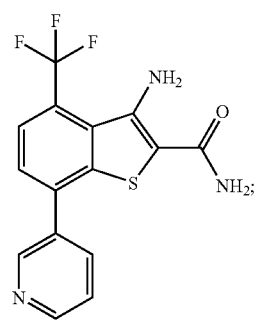

3-Amino-7-pyridin-4-yl-4-trifluoromethyl-benzo[b]thiophene-2-carboxylic acid amide

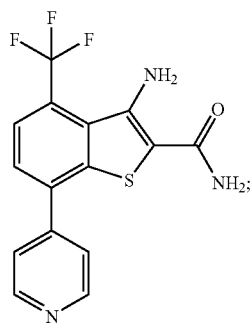

3-Amino-7-(3-cyano-phenyl)-4-trifluoromethyl-benzo[b]thiophene-2-carboxylic acid amide

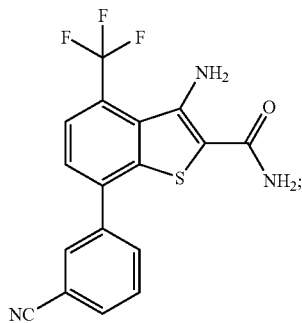

3-Amino-7-(4-cyano-phenyl)-4-trifluoromethyl-benzo[b]thiophene-2-carboxylic acid amide

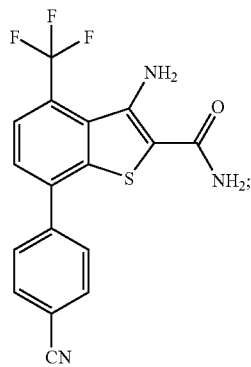

3-Amino-7-(3-hydroxy-phenyl)-4-trifluoromethyl-benzo[b]thiophene-2-carboxylic acid amide

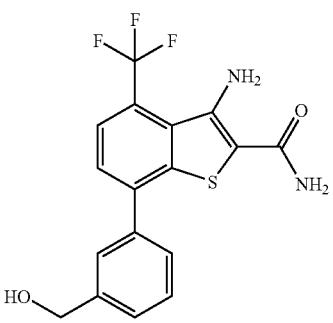

3-Amino-7-(4-aminomethyl-phenyl)-4-trifluoromethyl-benzo[b]thiophene-2-carboxylic acid amide

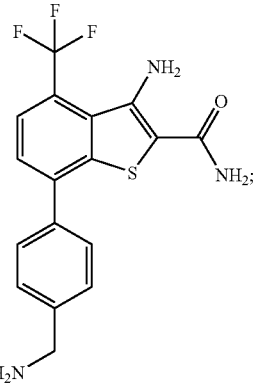

3-Amino-7-((E)-2-carbamoyl-vinyl)-4-trifluoromethyl-benzo[b]thiophene-2-carboxylic acid amide

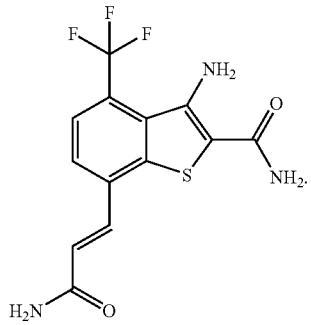

The following compound was prepared as described in Example 16 using 2-fluoro-3-iodo-6-ethoxybenzonitrile in place of 2-fluoro-3-iodo-6-trifluoromethylbenzonitrile:
3-Amino-4-ethoxy-7-furan-3-yl-benzo[b]thiophene-2-carboxylic acid amide

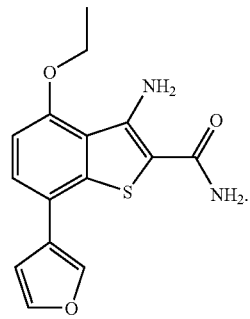

Example 17

Synthesis of 3-amino-4-ethoxy-5,7-diiodo-benzo[b]thiophene-2-carboxylic acid amide

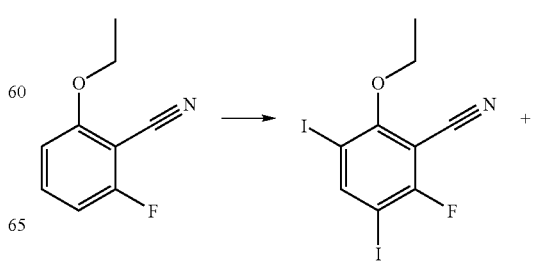

-continued

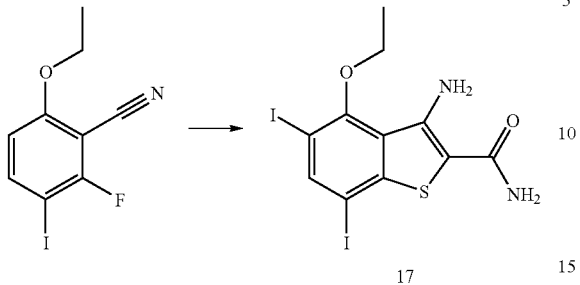

To a solution of 2M lithium diisopropylamide in heptane/THF/ethylbenzene (1.94 mL, 3.88 mmol) in 8 mL of dry THF under $N_2$ at −78° C. was added 2-fluoro-6-ethoxybenzonitrile (534.5 mg, 3.236 mmol) in 2 mL of dry THF. The mixture was stirred at −78° C. for 60 min, followed by the addition of iodine (1070 mg, 4.216 mmol) in 2 mL of dry THF. The reaction mixture was stirred at −78° C. for 2 h and 18 h at room temperature. The reaction mixture was then concentrated and a solution of $Na_2S_2O_3$ was added to the residue. The mixture was extracted with EtOAc and the organic layer was separated and washed with water and brine. The organic layer was dried over anhydrous $MgSO_4$, filtered and concentrated. The residue was purified by silica gel chromatography eluting with 0-5% EtOAc/hexane. The earlier fractions were collected and concentrated to afford 70 mg (5.2%) of 2-fluoro-3,5-diiodo-6-ethoxybenzonitrile as an off-white solid The later fractions were collected and concentrated to afford 395 mg (41.9%) of 2-fluoro-3-iodo-6-ethoxybenzonitrile as an off-white solid.

The above diiodo benzonitrile intermediate (70 mg, 0.168 mmol) was dissolved in 2 mL of MeOH, followed by the addition of 2-mercaptoacetamide (100 mg/mL in MeOH-ammonia solution) (0.184 mL, 0.201 mmol) and 0.5M sodium methoxide in MeOH (0.67 mL, 0.336 mmol). The reaction mixture was stirred at room temperature for 18 h and then was concentrated and the residue was purified by silica gel chromatography eluting with 2-5% MeOH/$CH_2Cl_2$. The product fractions were collected and concentrated to afford 10 mg (12.2%) of the title compound as a yellow solid.

Example 18

Synthesis of 3-Amino-4-ethoxy-7-(1H-imidazol-4-yl)-benzo[b]thiophene-2-carboxylic acid amide

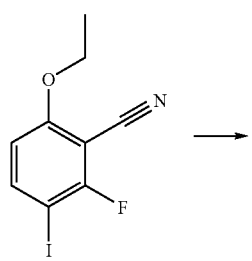

-continued

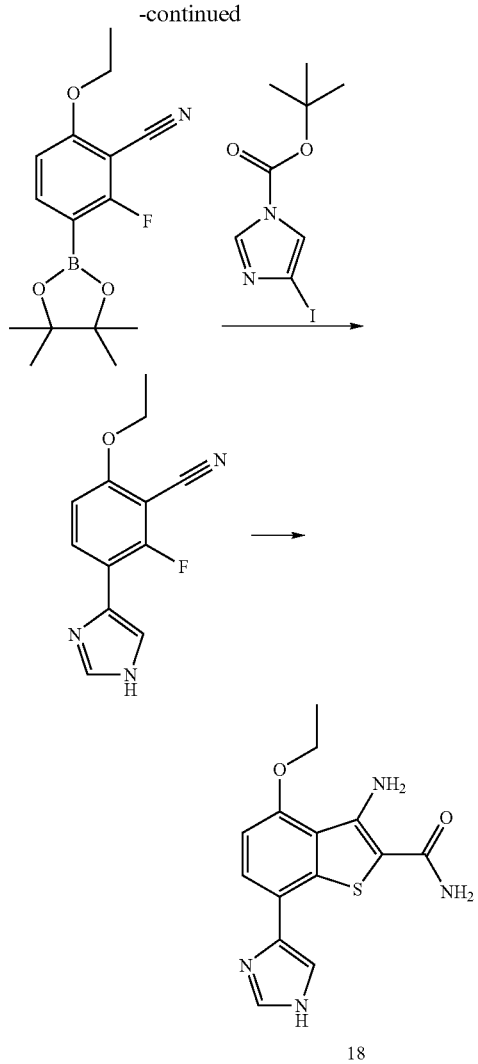

To a solution of 2 M n-BuLi in pentane (0.21 mL, 0.413 mmol) in 1 mL of dry THF under $N_2$ at −78° C. was added 2-fluoro-3-iodo-6-ethoxybenzonitrile (100 mg, 0.344 mmol) in 1 mL of dry THF. The mixture was stirred at −78° C. for 2 h, followed by the addition of bis(pinacolato)diboron (131 mg, 0.516 mmol) in 1 mL of dry THF. The reaction mixture was stirred at −78° C. for 2 h, then warmed up and stirred at room temperature for 18 h. The reaction mixture was concentrated and the residue was purified by silica gel chromatography eluting with 10-40% EtOAc/hexane. The product fractions were collected and concentrated to afford 60 mg (60%) of 6-ethoxy-2-fluoro-3-(4,4,5,5-tetramethyl-[1,3,2]dioxaborolan-2-yl)-benzonitrile as an off-white solid.

To a flask was added 4-iodo-1H-imidazole (500 mg, 3.402 mmol) in 100 mL of THF followed by the addition of di-tert-butyl dicarbonate (1.485 g, 6.804 mmol) and 5 mL of saturated $NaHCO_3$ solution. The reaction mixture was stirred at room temperature for 18 h and then diluted with EtOAc, and washed with $H_2O$ and brine. The organic phase was dried over anhydrous $MgSO_4$, filtered and concentrated. The residue was purified by silica gel chromatography eluting with 0-10% EtOAc/hexane. The product fractions were collected and concentrated to afford 388 mg (46.2%) of 4-iodo-imidazole-1-carboxylic acid tert-butyl ester as a white solid.

To a sealed tube was added the above tert-butyl ester intermediate (25.5 mg, 0.103 mmol), 6-ethoxy-2-fluoro-3-(4,4,5,5-tetramethyl-[1,3,2]dioxaborolan-2-yl)-benzonitrile (60 mg, 0.206 mmol) and tetrakis(triphenylphosphine)palladium(0) (23.85 mg, 0.0206 mmol) in 1 mL of dimethoxyethane, followed by the addition of 0.5 mL of 20% $Na_2CO_3$. The mixture was heated at 85° C. for 4 h. LCMS showed both de-boc and boc-protected imidazole compounds formed. The reaction mixture was filtered, concentrated and the residue was purified by silica gel chromatography eluting with 2-5% MeOH/$CH_2Cl_2$. The boc-protected intermediate was not found during the column process, the de-boc intermediate was found and the fractions were collected and concentrated to afford 11 mg (46.1%) of 6-ethoxy-2-fluoro-3-(1H-imidazol-4-yl)-benzonitrile.

To a sealed tube was added the above benzonitrile intermediate (11 mg, 0.0476 mmol) in 0.8 mL of MeOH, followed by the addition of 2-mercaptoacetamide (100 mg/mL in MeOH-ammonia solution) (0.4 mL, 0.439 mmol) and 0.5M sodium methoxide in MeOH (0.8 mL, 0.4 mmol). The reaction mixture was stirred at 80° C. for 48 h. The reaction mixture was concentrated and the residue was purified by silica gel chromatography eluting with 5% 2M $NH_3$ in MeOH/$CH_2Cl_2$. The product fractions were collected and concentrated to afford 10 mg (69.5%) of the title compound as an off-white solid.

The following compound was prepared by the procedure described in Example 18, using 2-iodoimidazole in place of 4-iodo-imidazole-1-carboxylic acid tert-butyl ester:

3-Amino-4-ethoxy-7-(1H-imidazol-2-yl)-benzo[b]thiophene-2-carboxylic acid amide

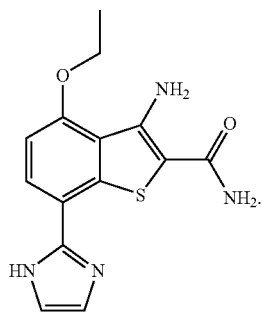

Example 19

Synthesis of 3-amino-5-phenyl-benzo[b]thiophene-2-carboxylic acid amide

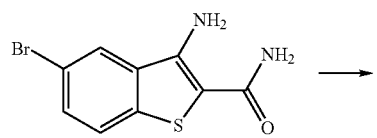

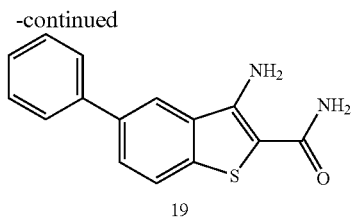

19

To a stirred solution of 3-amino-5-bromo-benzo[b]thiophene-2-carboxylic acid amide (90 mg, 0.33 mmol) in DMF (5 mL) was added phenylboronic acid (1.2 eq., 50 mg) at room temperature, under nitrogen. The resulting mixture was degassed and placed under nitrogen after which time sodium carbonate (1.2 eq., 43 mg) and Pd(Ph$_3$)$_4$ (0.4 eq., 155 mg) were added. The reaction was degassed again and warmed to 80° C. overnight, under nitrogen. Upon cooling to room temperature, the reaction was concentrated to dryness and the remaining residue was purified via flash column chromatrography (5 g SiO$_2$, 0-40% EtOAc/dichloromethane). The product-containing fractions were concentrated to give the product which was still contaminated. The brown solid was diluted with 1:1 CH$_3$CN/H$_2$O and the remaining solids were removed via filtration. The filtrate was re-purified using preparatory reverse phase HPLC to give 7.4 mg (8%) of the title compound as a white solid.

Example 20

Synthesis of 3-amino-7-phenyl-benzo[b]thiophene-2-carboxylic acid amide

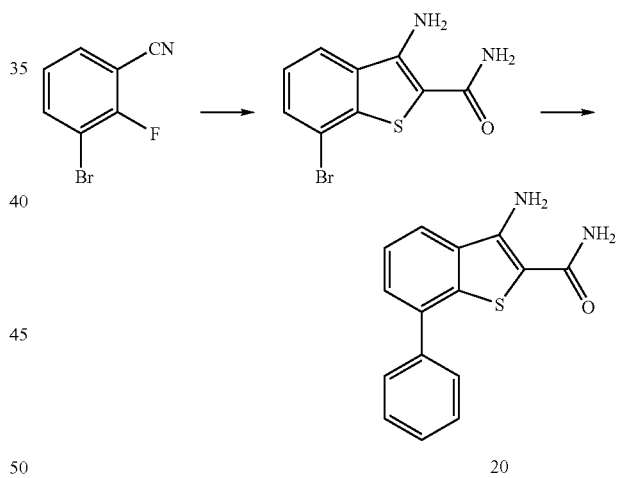

20

To a stirred solution of 3-bromo-2-fluoro-benzonitrile (2 g, 10 mmol) in DMF (50 mL) was added 2-mercaptoacetamide (1.2 eq., 12 mL, 100 mg/mL in MeOH-ammonia solution) followed by sodium methoxide (1.2 eq., 24 mL, 0.5 M in MeOH) at room temperature under nitrogen. After 2 h, the resulting homogenous yellow solution was warmed to 70° C. for 17 h. Upon cooling to room temperature, the resulting dark green reaction mixture was concentrated to give a green solid. This solid was diluted with MeOH and collected via filtration to give 2.0 g (74%) of 3-amino-7-bromo-benzo[b]thiophene-2-carboxylic acid amide.

A flask was charged with the above amide (0.1 g, 0.37 mmol) and 1,4-dioxane (5 mL).

The flask was degassed with nitrogen/house vacuum. 2-(di-t-Butylphosphino)biphenyl catalyst (5 mg) was added, followed by tetrakis(triphenylphosphine)palladium(0) (5 mg), phenylboronic acid (1.2 eq., 56 mg) and potassium fluoride (3.3 eq., 71 mg). The flask was degassed again (nitrogen/house vacuum). The reaction was stirred at room temperature for 3 h after which time it was warmed to 80° C. and stirred overnight. Upon cooling to room temperature, the reaction was diluted with 10% Na$_2$CO$_3$ solution (10 mL) and EtOAc (10 mL). The layers were separated and the aqueous phase was extracted with EtOAc (2×10 mL). The combined organics were dried (MgSO$_4$), filtered and concentrated. The remaining residue was redissolved in MeOH and treated with SiO$_2$ (~0.8 g) and purified via silica gel chromatography. The product-containing fractions were concentrated to give a yellowish solid which was re-purified via preparatory reverse phase HPLC to give 6.4 mg (6.5%) of the title compound as a white solid.

The following compounds were prepared using the procedure described in Example 20 and the appropriate aryl or heteroaryl boronic acid intermediate:

3-Amino-7-biphenyl-4-yl-benzo[b]thiophene-2-carboxylic acid amide

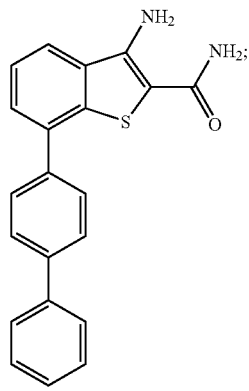

3-Amino-7-furan-3-yl-benzo[b]thiophene-2-carboxylic acid amide

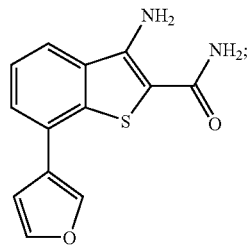

3-Amino-7-(4-methoxy-phenyl)-benzo[b]thiophene-2-carboxylic acid amide

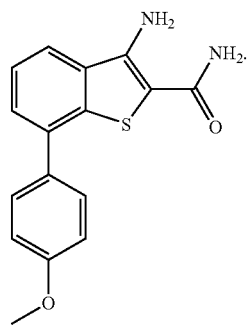

Example 21

Synthesis of morpholine-4-[2-(3-amino-2-carbamoyl-4-cyclopentylmethoxy-benzo[b]thiophen-6-yl)-ethyl]-carboxylic acid amide

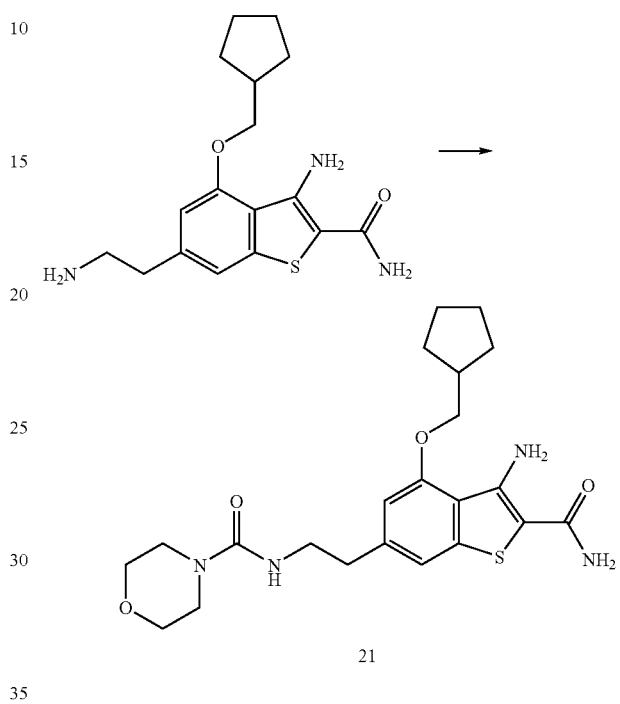

To a stirred solution of 3-amino-6-(2-amino-ethyl)-4-cyclopentylmethoxy-benzo[b]thiophene-2-carboxylic acid amide (11) (HCl salt form, 0.060 g, 0.16 mmol) and N,N-diisopropylethylamine (0.11 mL, 0.65 mmol) in DMF (1 mL) was added morpholinyl carbonyl chloride (0.04 mL, 0.3 mmol). It was stirred overnight and then diluted with water. The precipitates were filtered, washed with water, and dried in vacuo to give the title compouund (0.061 g, 84%).

Example 22

Synthesis of 3-amino-4-cyclopentylmethoxy-6-(2-methanesulfonylamino-ethyl)-benzo[b]thiophene-2-carboxylic acid amide

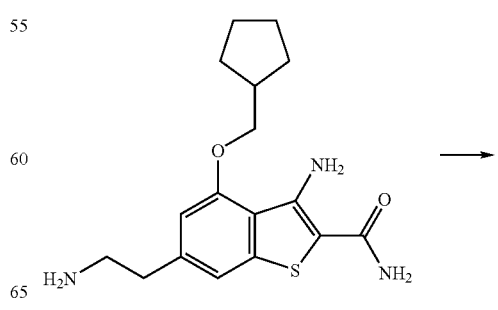

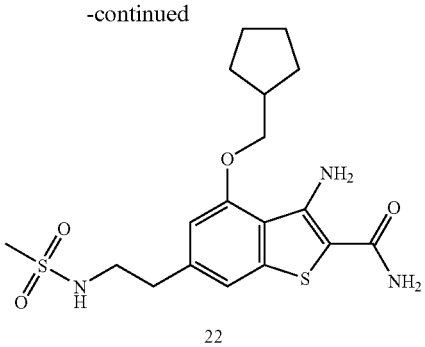

22

To a stirred solution of 3-amino-6-(2-amino-ethyl)-4-cyclopentylmethoxy-benzo[b]thiophene-2-carboxylic acid amide (11) (HCl salt form, 0.100 g, 0.270 mmol) in pyridine (1 mL) at 0° C. was added methanesulfonyl chloride (0.08 mL, 1 mmol). It was allowed to warm to room temperature and stirred overnight. It was diluted with water, extracted with dichloromethane, washed with brine, dried with sodium sulfate, and concentrated. The residue was purified by preparatory thin layer chromatography to afford the title compound (0.021 g, 19%).

Example 23

Synthesis of 3-amino-4-cyclopentylmethoxy-6-(2-ureido-ethyl)-benzo[b]thiophene-2-carboxylic acid amide

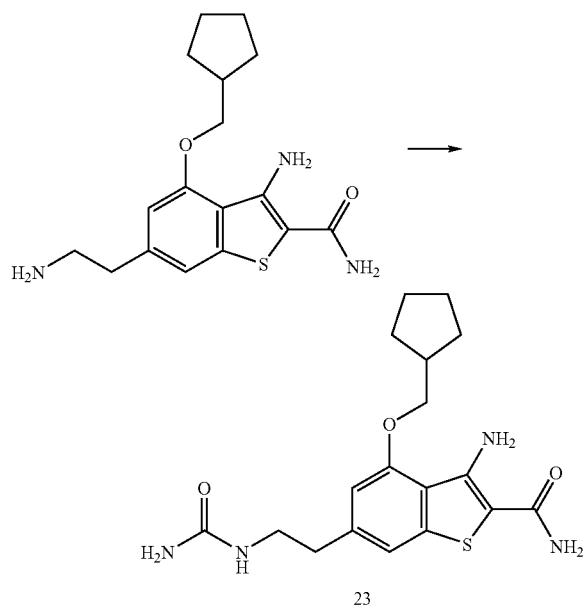

23

To a stirred solution of 3-amino-6-(2-amino-ethyl)-4-cyclopentylmethoxy-benzo[b]thiophene-2-carboxylic acid amide (11) (HCl salt form, 0.065 g, 0.18 mmol) and triethylamine (0.07 mL, 0.5 mmol) in DMF (1 mL) at 0° C. was added TMSNCO (1.35 mL, 10.0 mmol). The reaction was allowed to warm to room temperature and stirred for 24 h. It was slowly quenched with water (0.5 mL) and the precipitates were removed by filtration. The filtrate was concentrated and the residue was purified by preparatory thin layer chromatography to afford the title compound (0.010 g, 15%).

Example 24

Synthesis of 3-amino-4-cyclopentylmethoxy-6-(2-guanidino-ethyl)-benzo[b]thiophene-2-carboxylic acid amide

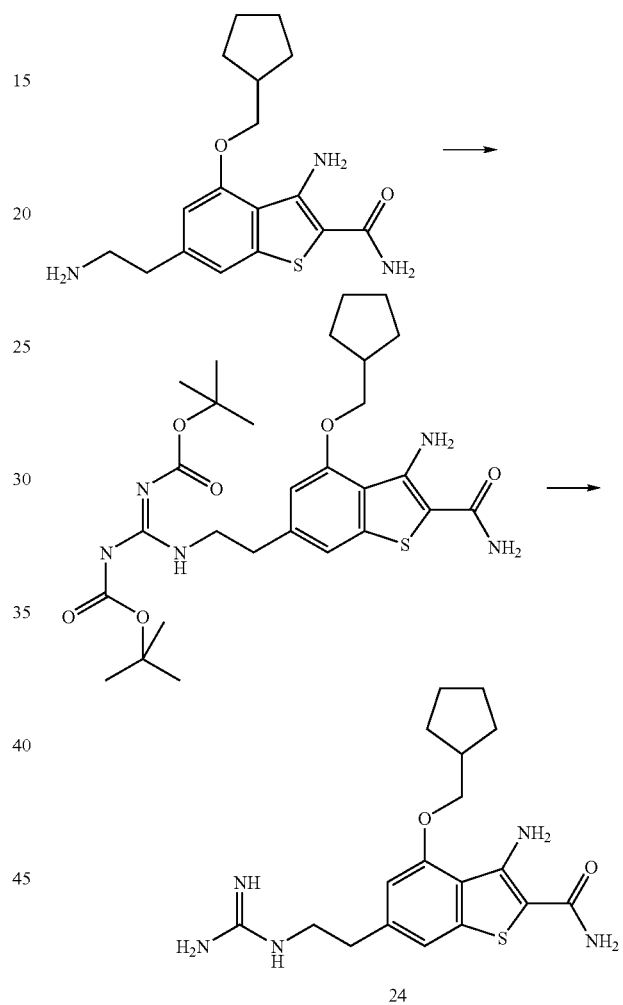

24

A mixture of 3-amino-6-(2-amino-ethyl)-4-cyclopentylmethoxy-benzo[b]thiophene-2-carboxylic acid amide (11) (HCl salt form, 0.10 g, 0.27 mmol), 1,3-di-boc-2-methyl-isothiourea (0.087 mg, 0.30 mmol) and triethylamine (0.15 mL, 1.1 mmol) in DMF (1 mL) was stirred at room temperature for 24 h. The solvent was removed and chromatography on silica gel afforded the 3-amino-4-cyclopentylmethoxy-6-(2-N',N''-di-tert-butoxycarbonyl-guanidino-ethyl)-benzo[b]thiophene-2-carboxylic acid amide (0.091 g, 58%).

To a solution of the above amide (0.060 g, 0.10 mmol) in THF (1 mL) was added HCl (4N in dioxane, 3 mL) and the reaction mixture was allowed to sit overnight. The solvent was removed and the residue was recrystallized from dioxane/MeOH to afford the title compound as the HCl salt (0.015 g, 35%).

Example 25

Synthesis of [2-(3-amino-2-carbamoyl-4-cyclopentylmethoxy-benzo[b]thiophen-6-yl)-ethyl]-carbamic acid methyl ester

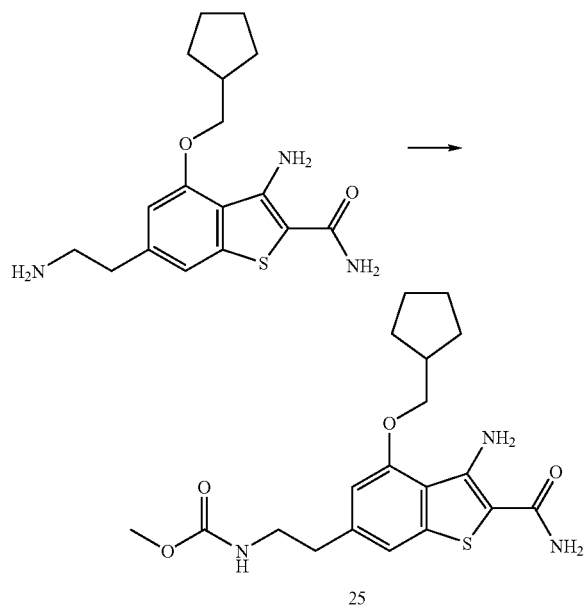

To a stirred solution of 3-amino-6-(2-amino-ethyl)-4-cyclopentylmethoxy-benzo[b]thiophene-2-carboxylic acid amide (11) (HCl salt form, 0.050 g, 0.14 mmol) and triethylamine (0.07 mL, 0.5 mmol) in DMF (1 mL) at 0° C. was added methyl-chloroformate (0.02 mL, 0.3 mmol). The reaction was allowed to warm to room temperature and stirred for 1 h. The reaction was quenched with MeOH and the solvent was removed under reduced pressure. The residue was purified by flash silica gel chromatography to afford the title compound (0.025 g, 47%).

Assessment of Biological Properties

The inhibition of IKKα and IKKβ by the compounds of the present invention was determined with the following assay that measures the phosphorylation of the IκBα substrate by the respective kinases. The enzymes used in the assay were N-terminally flag-tagged versions of the human IKKβ or IKKα and the substrate was a GST fusion protein with IκBα (amino acids 1-54).

The reaction mixtures (60 μl) contained 20 mM HEPES pH 7.5, 10 mM $MgCl_2$, 2 mM $MnCl_2$, 100 mM NaCl, 100 μM $Na_3VO_4$, 20 mM β-glycerophosphate, 1 mM DTT, 2% DMSO, 250 nM ATP, 0.4 nM [$^{33}$P]ATP (specific activity, 3000 Ci/mmol), IκBα substrate, IKK enzyme and test compound. The reaction mixtures contained either 3.6 μg/ml IKKα and 245 μg/ml IκBα or 0.9 μg/ml IKKβ and 53 μg/ml IκBα.

Reactions were initiated by adding a solution of IκBα substrate and ATP to polypropylene plates containing IKK enzyme that was pre-incubated for 5 minutes with test compound. Then the reaction mixtures were incubated for 1 hour at 25° C., placed on ice and quenched by the addition of 150 μl 10% trichloroacetic acid and 5% disodium pyrophosphate. After mixing, the entire contents of the quenched reaction mixtures were transferred to a pre-wetted Packard UniFilter filtration plate, aspirated and washed 6 times with 250 μl of $ddH_2O$ using the Packard Filtermate Harvester. Filtration plates were then air dried, supplemented with 40 μl of Microscint 20 scintillation fluid and the $^{33}$P-labeled reaction products were quantified using the Packard Top-Count scintillation counter.

Compounds were tested in three-fold serial dilutions and inhibitor concentrations to achieve 50% inhibition of enzyme activity (i.e., $IC_{50}$) were derived from dose-reponse curves using SAS software (SAS Institute, Cary N.C.). A non-linear regression analysis based on the Hill equation was applied to the percent inhibition versus concentration data. In all cases, compound concentrations were verified by HPLC.

Compounds in Table I in the Detailed Description of the Invention section were all evaluated in the assay for IKKβ inhibition and had $IC_{50}$'s of 10 μM or below. Compounds in Table II listed below had $IC_{50}$'s below 0.1 μM in this assay.

The invention claimed is:
1. A compound chosen from:
   3-Amino-6-(4-amino-piperidin-1-yl)-4-(2-dimethylamino-ethoxy)-benzo[b]thiophene-2-carboxylic acid amide;
   3-Amino-6-(4-amino-piperidin-1-yl)-4-(2,2,2-trifluoroethoxy)-benzo[b]thiophene-2-carboxylic acid amide;
   3-Amino-4-cyclopentyloxy-benzo[b]thiophene-2,7-dicarboxylic acid diamide;
   3-Amino-6-(4-amino-piperidin-1-yl)-4-(2-morpholin-4-yl-ethoxy)-benzo[b]thiophene-2-carboxylic acid amide;
   3-Amino-6-(4-amino-piperidin-1-yl)-4-(pyridin-4-ylmethoxy)-benzo[b]thiophene-2-carboxylic acid amide;
   3-Amino-6-(4-amino-piperidin-1-yl)-4-(2-benzylaminoethoxy)-benzo[b]thiophene-2-carboxylic acid amide;
   3-Amino-6-(4-amino-piperidin-1-yl)-4-ethoxy-benzo[b]thiophene-2-carboxylic acid amide;
   3-Amino-4-cyclopentylmethoxy-benzo[b]thiophene-2,7-dicarboxylic acid diamide;
   3-Amino-4-cyclobutoxy-benzo[b]thiophene-2,7-dicarboxylic acid diamide;
   3-Amino-4-cyclopropylmethoxy-benzo[b]thiophene-2,7-dicarboxylic acid diamide;
   3-Amino-4-ethoxy-6-(4-hydroxy-piperidin-1-yl)-benzo[b]thiophene-2-carboxylic acid amide;
   3-Amino-6-(4-amino-piperidin-1-yl)-4-(pyridin-3-ylmethoxy)-benzo[b]thiophene-2-carboxylic acid amide;
   3-Amino-4-ethoxy-benzo[b]thiophene-2,7-dicarboxylic acid diamide;
   3-Amino-4-cyclobutylmethoxy-benzo[b]thiophene-2,7-dicarboxylic acid diamide;
   3-Amino-4-cyclohexylmethoxy-benzo[b]thiophene-2,7-dicarboxylic acid diamide;
   3-Amino-4-propoxy-benzo[b]thiophene-2,7-dicarboxylic acid diamide;
   3-Amino-6-(2-amino-ethyl)-4-cyclopentylmethoxy-benzo[b]thiophene-2-carboxylic acid amide;
   3-Amino-4-methoxy-benzo[b]thiophene-2,7-dicarboxylic acid diamide;
   3-Amino-4-(2-hydroxy-ethoxy)-benzo[b]thiophene-2,7-dicarboxylic acid diamide;
   3-Amino-4-isopropoxy-benzo[b]thiophene-2,7-dicarboxylic acid diamide;
   3-Amino-4-ethoxy-5,7-diiodo-benzo[b]thiophene-2-carboxylic acid amide;

3-Amino-4-ethoxy-7-furan-3-yl-benzo[b]thiophene-2-carboxylic acid amide;
3-Amino-7-(4-cyano-phenyl)-4-trifluoromethyl-benzo[b]thiophene-2-carboxylic acid amide;
3-Amino-4-benzyloxy-benzo[b]thiophene-2,7-dicarboxylic acid diamide;
3-Amino-4-ethoxy-7-iodo-benzo[b]thiophene-2-carboxylic acid amide;
3-Amino-7-furan-3-yl-4-trifluoromethyl-benzo[b]thiophene-2-carboxylic acid amide;
3-Amino-4-cyclopentylmethoxy-6-[2-(diaminomethyl-amino)-ethyl]-benzo[b]thiophene-2-carboxylic acid amide;
3-Amino-7-iodo-4-trifluoromethyl-benzo[b]thiophene-2-carboxylic acid amide;
3-Amino-6-(4-amino-piperidin-1-yl)-4-(2-benzenesulfonylamino-ethoxy)-benzo[b]thiophene-2-carboxylic acid amide;
3-Amino-6-(4-amino-piperidin-1-yl)-4-benzyloxy-benzo[b]thiophene-2-carboxylic acid amide;
3-Amino-7-furan-3-yl-benzo[b]thiophene-2-carboxylic acid amide;
3-Amino-7-((Z)-2-carbamoyl-vinyl)-4-trifluoromethyl-benzo[b]thiophene-2-carboxylic acid amide;
3-Amino-4-phenethyloxy-benzo[b]thiophene-2,7-dicarboxylic acid diamide;
3-Amino-7-pyridin-4-yl-4-trifluoromethyl-benzo[b]thiophene-2-carboxylic acid amide;
3-Amino-6-(4-amino-piperidin-1-yl)-4-fluoro-benzo[b]thiophene-2-carboxylic acid amide;
3-Amino-6-(2-amino-ethyl)-4-ethoxy-benzo[b]thiophene-2-carboxylic acid amide;
3-Amino-6-(2-amino-ethyl)-4-(2,2,2-trifluoro-ethoxy)-benzo[b]thiophene-2-carboxylic acid amide;
3-Amino-6-(2-amino-ethyl)-4-cyclopentyloxy-benzo[b]thiophene-2-carboxylic acid amide;
{2-[3-Amino-2-carbamoyl-4-(2,2,2-trifluoro-ethoxy)-benzo[b]thiophen-6-yl]-ethyl}-carbamic acid methyl ester;
3-Amino-4-(2-amino-ethoxy)-6-(4-amino-piperidin-1-yl)-benzo[b]thiophene-2-carboxylic acid amide;
4-(2-Acetylamino-ethoxy)-3-amino-6-(4-amino-piperidin-1-yl)-benzo[b]thiophene-2-carboxylic acid amide;
3-Amino-6-(4-amino-piperidin-1-yl)-4-methylsulfanyl-benzo[b]thiophene-2-carboxylic acid amide;
or the pharmaceutically acceptable salts or acids thereof.

2. A compound chosen from:
3-Amino-6-(4-amino-piperidin-1-yl)-4-(2-dimethylamino-ethoxy)-benzo[b]thiophene-2-carboxylic acid amide;
3-Amino-6-(4-amino-piperidin-1-yl)-4-(2,2,2-trifluoro-ethoxy)-benzo[b]thiophene-2-carboxylic acid amide;
3-Amino-4-cyclopentyloxy-benzo[b]thiophene-2,7-dicarboxylic acid diamide;
3-Amino-6-(4-amino-piperidin-1-yl)-4-(2-morpholin-4-yl-ethoxy)-benzo[b]thiophene-2-carboxylic acid amide;
3-Amino-6-(4-amino-piperidin-1-yl)-4-(pyridin-4-ylmethoxy)-benzo[b]thiophene-2-carboxylic acid amide;
3-Amino-6-(4-amino-piperidin-1-yl)-4-ethoxy-benzo[b]thiophene-2-carboxylic acid amide;
3-Amino-6-(4-amino-piperidin-1-yl)-4-(2-benzylamino-ethoxy)-benzo[b]thiophene-2-carboxylic acid amide;
3-Amino-4-cyclopentylmethoxy-benzo[b]thiophene-2,7-dicarboxylic acid diamide;
3-Amino-4-cyclobutoxy-benzo[b]thiophene-2,7-dicarboxylic acid diamide;
3-Amino-4-cyclopropylmethoxy-benzo[b]thiophene-2,7-dicarboxylic acid diamide;
3-Amino-6-(2-amino-ethyl)-4-ethoxy-benzo[b]thiophene-2-carboxylic acid amide;
3-Amino-6-(2-amino-ethyl)-4-ethoxy-benzo[b]thiophene-2-carboxylic acid amide;
3-Amino-6-(2-amino-ethyl)-4-(2,2,2-trifluoro-ethoxy)-benzo[b]thiophene-2-carboxylic acid amide;
3-Amino-6-(2-amino-ethyl)-4-cyclopentyloxy-benzo[b]thiophene-2-carboxylic acid amide;
3-Amino-4-(2-amino-ethoxy)-6-(4-amino-piperidin-1-yl)-benzo[b]thiophene-2-carboxylic acid amide;
4-(2-Acetylamino-ethoxy)-3-amino-6-(4-amino-piperidin-1-yl)-benzo[b]thiophene-2-carboxylic acid amide
or the pharmaceutically acceptable salts, thereof.

3. A pharmaceutical composition containing a pharmaceutically effective amount of a compound according to claim 1 or 2 and one or more pharmaceutically acceptable carriers and/or adjuvants.

* * * * *